(12) United States Patent
Tal et al.

(10) Patent No.: US 11,413,436 B2
(45) Date of Patent: *Aug. 16, 2022

(54) DISRUPTING FIBRIN SHEATH FROM A HOST BLOOD VESSEL AND VISUALIZATION THEREOF

(71) Applicant: A V Medical Technologies Ltd, Tel-Aviv (IL)

(72) Inventors: Michael G. Tal, Woodbridge, CT (US); Ilan Carmel, Tel Mond (IL)

(73) Assignee: A V Medical Technologies Ltd., Tel-Aviv (IL)

( * ) Notice: Subject to any disclaimer, the term of this patent is extended or adjusted under 35 U.S.C. 154(b) by 89 days.

This patent is subject to a terminal disclaimer.

(21) Appl. No.: 16/787,412

(22) Filed: Feb. 11, 2020

(65) Prior Publication Data
US 2020/0171283 A1    Jun. 4, 2020

Related U.S. Application Data

(63) Continuation of application No. 14/413,264, filed as application No. PCT/IB2013/001895 on Jul. 8, 2013, now Pat. No. 10,561,827.
(Continued)

(51) Int. Cl.
*A61M 25/10* (2013.01)
*A61B 17/12* (2006.01)
(Continued)

(52) U.S. Cl.
CPC ....... *A61M 25/104* (2013.01); *A61B 17/1204* (2013.01); *A61B 17/12109* (2013.01);
(Continued)

(58) Field of Classification Search
CPC ...... A61M 25/104; A61M 5/007; A61M 5/14; A61M 25/0026; A61M 25/09;
(Continued)

(56) References Cited

U.S. PATENT DOCUMENTS

| 4,585,000 A | 4/1986 | Hershenson |
|---|---|---|
| 4,794,928 A | 1/1989 | Kletschka |

(Continued)

FOREIGN PATENT DOCUMENTS

| EP | 0770405 A2 | 5/1997 |
|---|---|---|
| WO | 9402196 A1 | 2/1994 |

(Continued)

OTHER PUBLICATIONS

Hacker et al. "Fibrin Sheath Angioplasty: A Technique to Prevent Superior Vena Cava Stenosis Secondary to Dialysis Catheters." The International Journal of Angiology : Official Publication of the International College of Angiology, Inc. 21.3 (2012): 129-134.
(Continued)

*Primary Examiner* — Amelie R Davis

(57) ABSTRACT

A percutaneous transluminal angioplasty (PTA) catheter may be configured to perform vein expansion and occlusion. A infusion port located proximal to the occlusion feature can be used to inject contrast enhancement agent as well as other substances. The catheter can be used especially advantageously in vascular regions associated with hemodialysis access.

18 Claims, 14 Drawing Sheets

Related U.S. Application Data

(60) Provisional application No. 61/752,649, filed on Jan. 15, 2013, provisional application No. 61/752,743, filed on Jan. 15, 2013, provisional application No. 61/669,284, filed on Jul. 9, 2012.

(51) Int. Cl.

| | | |
|---|---|---|
| *A61M 5/00* | (2006.01) | |
| *A61M 5/14* | (2006.01) | |
| *A61M 25/00* | (2006.01) | |
| *A61M 25/09* | (2006.01) | |
| *A61M 29/02* | (2006.01) | |
| *A61B 6/00* | (2006.01) | |
| *A61B 17/22* | (2006.01) | |

(52) U.S. Cl.
CPC .. *A61B 17/12136* (2013.01); *A61B 17/12168* (2013.01); *A61M 5/007* (2013.01); *A61M 5/14* (2013.01); *A61M 25/0026* (2013.01); *A61M 25/09* (2013.01); *A61M 25/1011* (2013.01); *A61M 29/02* (2013.01); *A61B 6/481* (2013.01); *A61B 6/504* (2013.01); *A61B 2017/22001* (2013.01); *A61B 2017/22082* (2013.01); *A61B 2017/22084* (2013.01); *A61M 2005/1403* (2013.01); *A61M 2025/105* (2013.01); *A61M 2025/1013* (2013.01); *A61M 2025/1052* (2013.01); *A61M 2025/1061* (2013.01); *A61M 2025/1079* (2013.01)

(58) Field of Classification Search
CPC .............. A61M 25/1011; A61M 29/02; A61M 2025/1052; A61M 2005/1403; A61M 2025/1061; A61M 2025/1079; A61B 17/1204; A61B 17/12168; A61B 17/12109; A61B 17/12136; A61B 2017/22082; A61B 2017/22084; A61B 6/504; A61B 6/481; A61B 2017/22001
See application file for complete search history.

(56) References Cited

U.S. PATENT DOCUMENTS

| | | |
|---|---|---|
| 5,069,673 A | 12/1991 | Shwab |
| 5,267,979 A | 12/1993 | Appling et al. |
| 5,306,247 A | 4/1994 | Pfenninger |
| 5,318,032 A | 6/1994 | Lonsbury et al. |
| 5,368,567 A | 11/1994 | Lee |
| 5,439,447 A | 8/1995 | Miraki |
| 5,693,088 A | 12/1997 | Lazarus |
| 5,836,967 A | 11/1998 | Schneider |
| 5,908,407 A | 6/1999 | Frazee et al. |
| 6,010,521 A | 1/2000 | Lee et al. |
| 6,017,323 A | 1/2000 | Chee |
| 6,022,336 A | 2/2000 | Zadno-Azizi et al. |
| 6,051,020 A | 4/2000 | Goicoechea et al. |
| 6,231,543 B1 | 5/2001 | Hegde et al. |
| 6,440,097 B1 | 8/2002 | Kupiecki |
| 6,485,500 B1 | 11/2002 | Kokish et al. |
| 6,544,217 B1 | 4/2003 | Gulachenski |
| 6,663,648 B1 | 12/2003 | Trotta |
| 7,195,611 B1 | 3/2007 | Simpson et al. |
| 7,873,404 B1 | 1/2011 | Patton |
| 8,532,749 B1 | 9/2013 | Patton |
| 2002/0143251 A1 | 10/2002 | Richardson et al. |
| 2003/0204236 A1 | 10/2003 | Letort |
| 2004/0068250 A1 | 4/2004 | Boutilette et al. |
| 2004/0116832 A1 | 6/2004 | Friedrich et al. |
| 2004/0122465 A1 | 6/2004 | McMurtry |
| 2006/0064058 A1 | 3/2006 | Coyle |
| 2006/0253071 A1 | 11/2006 | Zattera |
| 2007/0060882 A1 | 3/2007 | Tai |
| 2007/0129752 A1 | 6/2007 | Webler et al. |
| 2008/0221550 A1 | 9/2008 | Lee |
| 2009/0312827 A1 | 12/2009 | Stapleton |
| 2010/0198186 A1 | 8/2010 | Ackermann |
| 2010/0256506 A1 | 10/2010 | Mohl |
| 2011/0270373 A1 | 11/2011 | Sampognaro et al. |
| 2012/0110598 A1 | 5/2012 | Rastogi et al. |
| 2012/0265135 A1 | 10/2012 | Porter |
| 2012/0265287 A1 | 10/2012 | Sharma et al. |
| 2013/0172661 A1 | 7/2013 | Farnan et al. |
| 2014/0316263 A1 | 10/2014 | Murphy |
| 2015/0209557 A1 | 7/2015 | Tal et al. |

FOREIGN PATENT DOCUMENTS

| | | |
|---|---|---|
| WO | 9505862 A1 | 3/1995 |
| WO | 9942059 A2 | 8/1999 |
| WO | 0156645 A1 | 8/2001 |
| WO | 2012110598 A1 | 8/2012 |

OTHER PUBLICATIONS

Besarab et al. "Catheter Management in Hemodialysis Patients: Delivering Adequate Flow." Clinical Journal of the American Society of Nephrology, vol. 6: (2011): 227-234.
Dec. 12, 2013 International Search Report issued in International Application No. PCT/IB2013/001895.
Oct. 13, 2016 International Search Report issued in International Patent Application No. PCT/IB2016/053804.
Jul. 30, 2014 International Search Report issued in International Patent Application No. PCT/US2014/010752.
Apr. 22, 2015 International Search Report issued in International Patent Application No. PCT/IB2015/000010.

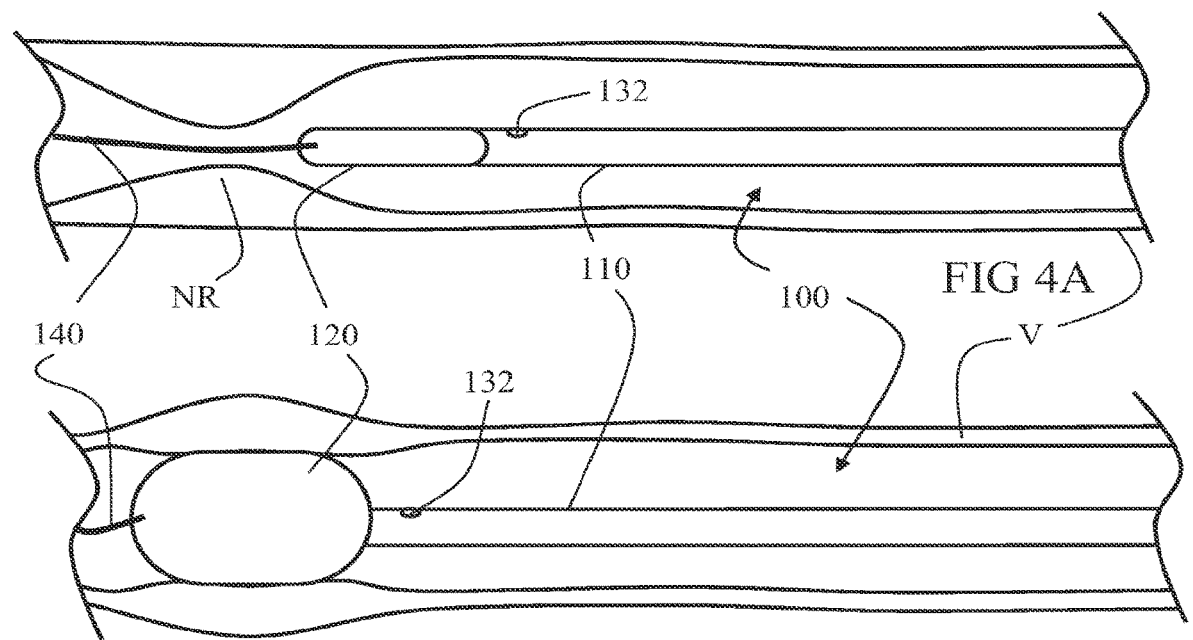
FIG 4A
FIG 4B
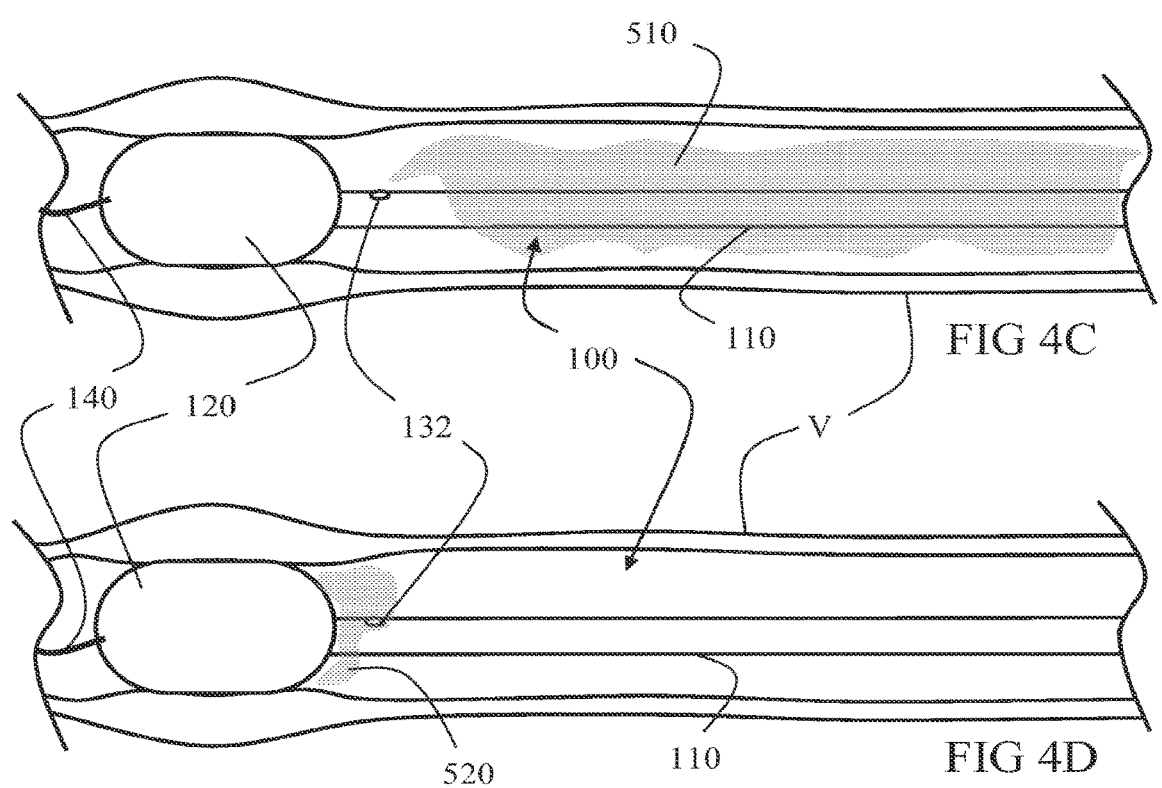
FIG 4C
FIG 4D

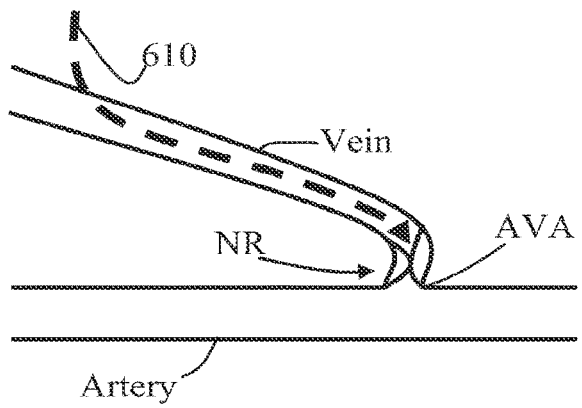
FIG 7A
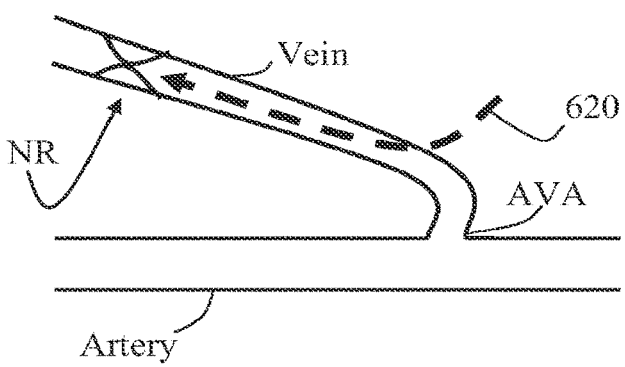
FIG 7B
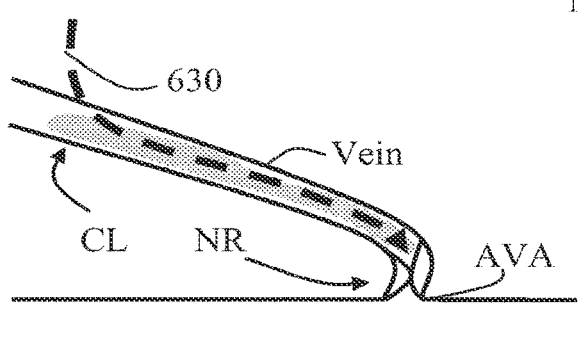
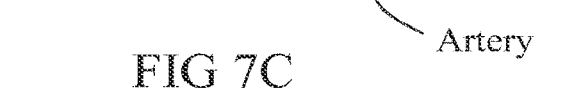
FIG 7C
FIG 7D

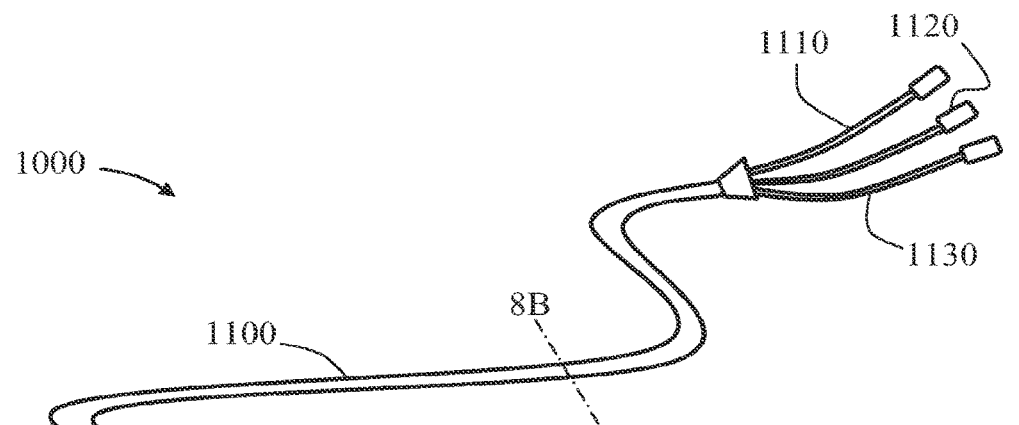
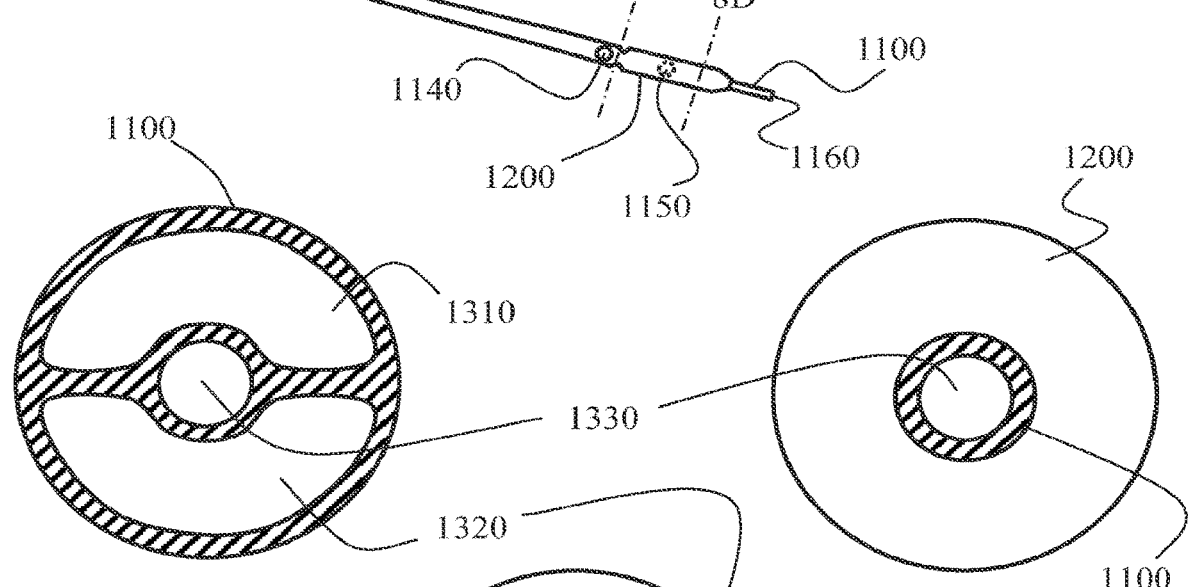
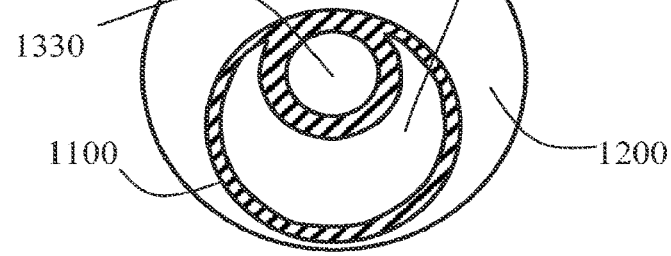
FIG 8A
FIG 8B
FIG 8C
FIG 8D ns, including, for example, the Kevlar balloon based Conquest® PTA dilatation catheter (of CR Bard; Covington, Ga.), provided in nominal inflation diameters between 5 mm and 12 mm, and with rated burst pressures between 20 atm and 30 atm.

DISRUPTING FIBRIN SHEATH FROM A HOST BLOOD VESSEL AND VISUALIZATION THEREOF

CROSS-REFERENCE TO RELATED APPLICATIONS

This application is a continuation of U.S. patent application Ser. No. 14/413,264 filed Jan. 7, 2015, which is a National Stage Application of PCT/IB2013/001895 filed Jul. 8, 2013, which claims benefit of and priority to U.S. Provisional Application No. 61/752,743 filed Jan. 15, 2013, U.S. Provisional Application No. 61/752,649 filed Jan. 15, 2013, and U.S. Provisional Application No. 61/669,284 filed Jul. 9, 2012. The disclosures of each of the foregoing applications are hereby incorporated by reference in their entirety herein.

FIELD AND BACKGROUND OF THE INVENTION

The present invention, in some embodiments thereof, relates to systems and methods for treating blood vessels or grafts, and in particular to dilatation balloon catheters for dilating and/or recanalizing occluded or narrowed vein portions and/or vascular accesses.

ESRD (end-stage renal disease) patients amount to about 3 million worldwide, out of which approximately 2 million undergo periodic hemodialysis treatments. Hemodialysis requires a vascular access, a site on the body where blood is removed and returned during the dialysis process. The most common accesses are the arteriovenous (AV) fistula, and the AV graft. Complications of clogging and stenosis occur with high percentages, causing low blood flow at the access site and risking the dialysis process. A regular checkup and assessment of the access is required. Once a problem of low blood flow is identified due to access narrowing, an angioplasty procedure is required to recover normal blood flow. If a blood clot is occluding the access, commonly associated with synthetic grafts, the treatments include thrombectomy and/or thrombolysis. Dialysis access procedures are performed several times per day per operator. Current techniques are time consuming and force the medical practitioner to extended exposures to x-ray radiation.

A venous flow obstruction or stenosis, commonly found in the graft-vein or vein-artery anastomosis of the arteriovenous fistula, causes slow down or obstruction of blood flow, which may result in the formation of thrombus within a graft. Stenotic vein portions may also be found at locations remote from the anastomosis such as in the brachicephalic vein. Usually mechanical thrombolysis means and/or administration of clot dissolving thrombolytic agents is used. After clot dissolution, the patient is typically analyzed under fluoroscopic imaging of the graft to identify and visualize residual venous stenosis. Angioplasty of the stenosed segment can then be performed, using dedicated high pressure dilatation balloon catheters, optionally followed with implanting a stent in order to keep opened areas that are prone to restenosis.

The cephalic vein or basilic vein, which are most common in vascular recanalization of hemodialysis accesses, are substantially large conduits, usually 3 to 6 mm in diameter, demanding high pressure dilatations of 15 atmospheres or more, and in some instances require the use of high pressure ultra-noncompliant dilatations of 25 atmospheres or more. Therefore, specially designed and sized angioplasty or PTA balloon catheters were developed for such specific indications, including, for example, the Kevlar balloon based Conquest® PTA dilatation catheter (of CR Bard; Covington, Ga.), provided in nominal inflation diameters between 5 mm and 12 mm, and with rated burst pressures between 20 atm and 30 atm.

Before and/or during the angioplasty procedure, blood thinners are administrated to prevent formation of blood clots in the conduit during prolonged angioplasty. The blood thinners in dialysis patients carry a risk of bleeding in different areas in the body including at the access sites to the fistula or graft. Having the option to reduce or eliminate the necessary dose of blood thinners will greatly improve patient safely as well as operators' convenience and satisfaction. Less time will be needed for hemostasis at the end of the procedure.

In order to position the balloon adjacent the stenosis and evaluate the result of the angioplasty, a contrast medium is administered to facilitate visualization under fluoroscopic imaging. In common practice, in order to administer the contrast medium adjacent the stenotic region following angioplasty, the dilatation balloon is withdrawn and is replaced with an occlusion balloon for blocking unwanted flow direction of the contrast medium. An occlusion balloon, as opposed to a high pressure dilatation balloon, is made substantially compliant in order to take a shape according to local surrounding boundaries. Inventor Michael Tal in U.S. Pat. No. 7,182,755 "METHOD AND APPARATUS FOR TREATMENT OF THROMBOSED HEMODIALYSIS ACCESS GRAFTS", the disclosures of which is fully incorporated herein by reference, describes a balloon catheter comprising "a catheter body with a compliant balloon secured at a distal end of the catheter body, a single aperture positioned proximally of the balloon, a first lumen extending through the catheter body and in fluid communication with the balloon for selectively inflating and deflating the balloon, and a second lumen extending through the catheter body and in fluid communication with the aperture for dispensing solution therethrough."

The need to replace the angioplasty balloon with an occlusion balloon for administering contrast medium is cumbersome and time consuming and even less efficient if further dilatation sessions are needed. This is especially important in angioplasty procedures involving the use of delivering or eluting drug with the angioplasty catheter, used for prevent or diminish restenosis in the recanalized vascular portion, with or without a stent deployed in-place, which usually involve repeated or continuous dilatation for prolonged durations greater than 1 minute, and more commonly 3 minutes or more.

Problems associated with current vascular access recanalization thus include: use of multiple catheters and multiple device exchanges, each associated with additional radiation to visualize position of each catheter; rapid blood flow in the access limits visualization of the blood vessels and requires repeated contrast injections and angiograms; risk of clot migration to artery when performing declotting procedure.

There is thus a need to introduce multi-functional balloon catheters dedicated to angioplasty and/or occlusion that also include means for fluids dispersion (medicaments and declotting agents, flushing media and/or contrast enhancing media) for facilitating improved techniques that can lower number of procedural steps, treatment time and radiation exposure. There is also a need to decrease overall amount of contrast enhancing media injected per session. There is also a need to inject contrast enhancing media into a clogged access for whole access visualization while declotting, therefore diminishing the risk of clot migration to the artery.

SUMMARY OF THE INVENTION

The present disclosure relates to dilatation balloon catheters such as a PTA (percutaneous transluminal angioplasty) balloon catheter, optionally of a high pressure type, optionally introducible as an over the wire catheter. The catheter possess the attribute of injecting fluid to the treated site through a dedicated opening located proximally to the balloon member, for introduction of fluids such as contrast enhancing material and/or medication. Fluid injection can be performed simultaneously while inflating or deflating the balloon, or while balloon is maintained inflated. Possibly, number of radiopaque markings is present to define the working length of the balloon and facilitate in balloon placement. In some embodiments, a single lumen is used, at least in part, both for fluids transfer and dispersion ("infusion") as well as for guide wire passage. In some such embodiments, a valve mechanism is used to sustain selective operability of the lumen so that fluids will disperse mostly or solely through the proximal dispersion opening rather than the guide wire distal exit opening. In one example, the catheter ends with a tip, optionally an atraumatic tip with a check-valve integrated inside the guide wire lumen distal to the injection opening to allow infusion of fluids with or without the guide wire. Such a device can be used for multiple function is sequence and/or in parallel, such as: performing high-pressure angioplasty in native arteriovenous dialysis fistulae or synthetic grafts; perform balloon dilatation and simultaneous contrast material injection; using smaller amounts of contrast enhancing material; decreasing use of angiograms and radiation exposure to staff and patient.

Catheters according to the present disclosures may be used also for embolectomy and declotting procedures. A device according to the present invention may include, though not necessarily, a relatively soft and compliant balloon fixed at the distal tip. The catheter possess the attribute of injecting fluid to the treated site through a dedicated opening proximal to the balloon for introduction of fluids such as clot dissolving material (such as TPA). Fluid injection can be performed simultaneously while inflating or deflating the balloon, or while balloon is maintained inflated. Such a device can be used for multiple function is sequence and/or in parallel, such as: performing balloon occlusion (possibly following dilatation) and simultaneous clot dissolving fluid injection; reducing the risk of clot migration to the arterial side during thrombectomy procedure and injection of contrast to the clogged access; using smaller amounts of contrast enhancing material; decreasing use of angiograms and radiation exposure to staff and patient.

According to an aspect of some embodiments of the present invention there is provided a dilatation balloon catheter which comprises an expandable chamber sized and configured to expand a vein lumen portion in a dialysis vascular access above a nominal size thereof. In some such embodiments, the vein is a cephalic or basilica vein, and/or the vascular access is an arteriovenous graft or an arteriovenous fistula. In some such embodiments, the nominal size is at least 3 mm or at least 10 mm. In some embodiments, the expandable chamber is configured to maintain a non-ruptured form under inflation pressures exceeding 20 atmospheres, in some embodiments exceeding 25 atmospheres. In some embodiments, such inflation pressures can be maintained continuously for at least 1 minute. This allows time, for example, for imaging a vascular region associated with dialysis access while the dilatation balloon remains inflated.

In some embodiments, the expandable chamber comprises an inflatable balloon. The inflatable balloon may be configured to maintain a non-ruptured form under continuous and/or repeated expansions under the inflation pressures for at least 3 minutes.

In some embodiments, the dilatation balloon catheter further comprises a guidewire lumen for allowing a guidewire to pass therethrough and exit through a guidewire exit port located distally to the infusion exit port.

In some embodiments, the dilatation balloon catheter comprises an infusion exit port located proximally to the expandable chamber for allowing a contrast enhancing fluid to exit the dilatation balloon catheter.

In some embodiments, the dilatation balloon catheter further comprises an infusion inlet port and an infusion lumen intercommunicating the infusion inlet port and the infusion exit port, the infusion inlet port is connectable to communicate with an interior of an appendix reservoir containing infusion material. The infusion material may comprise the contrast enhancing fluid. Alternatively or additionally, the infusion material may comprise at least one of: mitotic inhibitor, antimitotic agent, mitosis modulator, antineoplastic agent, antiproliferative agent, immunosuppressive agent, paclitaxel, sirolimus, zotarolimus, everolimus, Biolimus A9, anticoagulation agent and heparin. Alternatively or additionally, the infusion material may comprise at least one of: antiproleferative agent solvent, Cremophor EL, castor oil, ethanol, albumin, protamine sulfate, antiproliferative agent enhancer, antibiotics, and a vitamin.

In some embodiments, the infusion inlet port is further connectable to a source for continuously flowable flushing fluid.

In some embodiments, the dilatation balloon catheter further comprises a medication dispersion lumen for allowing a medication to pass therethrough and exit through a medication exit port located adjacent to the infusion exit port.

In some embodiments, the expandable chamber comprises a compliant layer expandable to take a form constrained by surrounding boundaries of the vein lumen portion, readily expanded above the nominal size, and to occlude the lumen portion from the contrast enhancing fluid passing between periphery thereof and the surrounding boundaries. Optionally, alternatively or additionally, the expandable chamber comprises a non-compliant layer expandable to form the vein lumen portion to an expanded size above the nominal size having predefined boundaries.

In some embodiments, the dilatation balloon catheter comprises a first independently inflatable balloon that includes a compliant layer and a second independently inflatable balloon that includes a non-compliant layer. In some embodiments, the expandable chamber comprises the second independently inflatable balloon and positioned proximally distanced to the first independently inflatable balloon. Optionally and alternatively, the expandable chamber comprises the second independently inflatable balloon disposed within the first independently inflatable balloon.

In some embodiments, any of the compliant layer, the non-compliant layer, the first independently inflatable balloon and the second independently inflatable balloon, are coated or impregnated with at least one of mitotic inhibitor, antimitotic agent, mitosis modulator, antineoplastic agent, antiproliferative agent, immunosuppressive agent, paclitaxel, sirolimus, zotarolimus, everolimus, Biolimus A9, anticoagulation agent, and heparin.

In some embodiments, the expandable chamber further comprises an expandable rigid spacer, optionally comprises a selectively expandable cage member, wherein the compliant layer is disposed between the spacer and the surrounding boundaries. In some such embodiments, the spacer comprises a self-expandable member provided in covering sheath, the self-expandable member is radially expandable when the covering sheath is proximally withdrawn.

In an aspect of some embodiments, there is provided a method which comprises at least one of the following steps, not necessarily in same order: inserting a dilatation balloon catheter in a narrowed vein lumen portion adjacent a dialysis vascular access through an opening in the dialysis vascular access; positioning the expandable chamber appositionally to the lumen portion; expanding the expandable chamber to expand the lumen portion to above the nominal size; applying the dilatation balloon catheter to occlude the expanded lumen portion; and administering contrast enhancing fluid through the infusion exit port.

Optionally, alternatively or additionally, the method comprises at least one of the following steps, not necessarily in same order: inserting a dilatation balloon catheter in a narrowed vein lumen portion of a non maturing fistula through an opening in the vein portion of the fistula; positioning the expandable chamber appositionally to the narrow segment of the non maturing fistula; expanding the expandable chamber to expand the lumen portion to above the nominal size; applying the dilatation balloon catheter to occlude the expanded lumen portion; infusing medication into the narrowed segment through the balloon over a prolonged period of time; and administering fluid through the infusion exit port continuously for at least 1 minute.

In some embodiments, the applying is comprised in the expanding.

In some embodiments, the applying and/or expanding comprises inflating the first independently inflatable balloon.

In some embodiments, the inflating includes elevating a pressure in the first independently inflatable balloon to a maximal pressure being at least 20 atmospheres, or in some cases at least 25 atmospheres. In some such embodiments, the maximal pressure is maintained and/or repeatedly obtained for at least 1 minute. In some such embodiments, the first independently inflatable balloon is coated or impregnated with a first anti-restenosis medication.

In some embodiments, the applying comprises expanding an expandable rigid spacer.

In some embodiments, the method further comprises: delivering a second anti-restenosis medication through the infusion exit port.

In some embodiments, the first anti-restenosis medication and/or the second anti-restenosis medication comprises at least one of a mitotic inhibitor, an antimitotic agent, a mitosis modulator, an antineoplastic agent, an antiproliferative agent, an immunosuppressive agent, paclitaxel, sirolimus, zotarolimus, everolimus, Biolimus A9, an anticoagulation agent, and heparin.

In some embodiments, the method further comprises: flushing the narrowed vein lumen portion with a continuous stream of flushing fluid through the infusion exit port.

A variety of methods are also provided.

In one implementation, a method of visualizing a vessel segment associated with dialysis treatment comprises selecting a hemodialysis patient having a hemodialysis vascular access path and/or other hemodialysis related vascular region in need of angiographic visualization and/or angioplasty treatment, inserting a catheter in a vessel of the selected hemodialysis patient, the catheter comprising an elongated shaft having an infusion lumen, an expandable dilatation chamber disposed on the elongated shaft, and one or more infusion openings in communication with the infusion lumen positioned proximally adjacent to the expandable dilatation chamber, positioning the expandable dilatation chamber at a narrowed or obstructed lumen segment at or near an arterial or venous anastomosis associated with an arteriovenous fistula and/or an arteriovenous graft, and expanding at least the expandable dilatation chamber to expand the narrowed or obstructed lumen segment above its nominal size. Then, using the same already inserted catheter, substantially occluding blood and other fluid flow through the expanded lumen segment, administering a radiographic contrast enhancing agent through the one or more infusion openings while maintaining the substantially occluded blood and other fluid flow, and radiographically imaging the vascular region at and/or around the arteriovenous fistula and/or arteriovenous graft proximal to the expanded lumen segment while maintaining the substantially occluded blood and other fluid flow.

In this implementation, the expandable dilatation chamber may comprise an inflatable balloon. The expandable dilatation chamber may be configured to maintain a non-ruptured state under a pressure of at least 20 atmospheres. The expandable dilatation chamber may be configured to maintain a non-ruptured state under a pressure of at least 20 atmospheres for at least one minute. The expanded dilatation chamber may perform both the expanding and the substantial occluding at the same time. The substantially occluding may comprise occluding the expanded lumen segment at least 95%. The method may further comprise visualizing the vascular region at and/or around the arteriovenous fistula and/or arteriovenous graft proximal to the expanded lumen segment with fluoroscopic imaging while the dilatation chamber remains expanded. Expanding the expandable dilatation chamber may comprise expanding an expandable rigid spacer. The method may comprise expanding an occlusion balloon provided on the catheter that is separate from the dilatation chamber to perform the occluding. The occlusion balloon may be proximally adjacent to the dilatation chamber. The dilatation chamber may be inside the occlusion balloon. The catheter may include a single infusion opening.

In another implementation, a method of treating a narrowed vein adjacent an arteriovenous anastomosis comprises inserting a balloon catheter in a vein lumen of a vein that is connected at an arteriovenous anastomosis to an artery, the balloon catheter comprising an elongated shaft having an infusion lumen, and an expandable dilatation balloon disposed along the elongated shaft. The method may continue by advancing the balloon catheter in the vein lumen toward the arteriovenous anastomosis until the expandable dilatation balloon reaches a narrowed vein segment, inflating the expandable dilatation balloon to open the narrowed vein segment, maintaining inflation of the expandable dilatation balloon to occlude the vein segment for a prolonged period, such as at least 1 minute for example, and administering a contrast enhancing fluid through an exit port of the infusion lumen while the expandable dilatation balloon remains inflated.

In another implementation, a method of treating a narrowed vein spaced upstream from an arteriovenous anastomosis comprises inserting a balloon catheter in a vein lumen of a vein that is connected at an arteriovenous anastomosis to an artery, the balloon catheter comprising an elongated shaft having an infusion lumen, and an expandable dilatation balloon disposed along the elongated shaft. The method may continue by advancing the balloon catheter away from the arteriovenous anastomosis until the expandable dilatation balloon reaches a narrowed vein segment, inflating the expandable dilatation balloon to open the narrowed vein segment, maintaining inflation of the expandable dilatation balloon to occlude the vein segment for a prolonged period, and administering a contrast enhancing fluid through an exit port of the infusion lumen towards the arteriovenous anastomosis and into the artery while the expandable dilatation balloon remains inflated.

In another implementation a method of treating a narrowed vein adjacent an arteriovenous anastomosis comprises inserting a balloon catheter in a vein lumen of a vein that is connected at an arteriovenous anastomosis to an artery, the balloon catheter comprising an elongated shaft having an infusion lumen, and an expandable dilatation balloon disposed along the elongated shaft. The method may continue by advancing the balloon catheter in the vein lumen toward the arteriovenous anastomosis until the expandable dilatation balloon reaches the arteriovenous anastomosis, inflating the expandable dilatation balloon at the arteriovenous anastomosis to block clotting material from entering the artery, maintaining inflation of the expandable dilatation balloon to occlude the arteriovenous anastomosis for a prolonged period, administering a contrast enhancing fluid through an exit port of the infusion lumen while the expandable dilatation balloon remains inflated, imaging the vein to locate blocked or narrowed vein lumen portions, and injecting a clot dissolving material through a portion of the balloon catheter and into the vein lumen at a location proximal to the expandable dilatation balloon.

In another implementation, a method of recanalizing a blocked arteriovenous graft comprises inserting a balloon catheter in a graft lumen or in a vein lumen of a vein that is connected by a graft to an artery, the balloon catheter comprising an elongated shaft having an infusion lumen, and an expandable dilatation balloon disposed along the elongated shaft. The method may continue by advancing the balloon catheter away from a venous anastomosis until the expandable dilatation balloon reaches an arterial anastomosis, inflating the expandable dilatation balloon at the arterial anastomosis to block clotting material from entering the artery, maintaining inflation of the expandable dilatation balloon to occlude the arteriovenous anastomosis for a prolonged period, administering a contrast enhancing fluid through an exit port of the infusion lumen while the expandable dilatation balloon remains inflated, imaging the graft to locate blocked or narrowed graft lumen portions, and injecting a clot dissolving material through a portion of the balloon catheter and into the graft lumen and vein lumen at a location proximal to the expandable dilatation balloon.

In another implementation, a method of treating a fibrin sheath associated with a long term implanted hemodialysis catheter comprises selecting a hemodialysis patient having a hemodialysis catheter positioned in a vascular access path extending along a jugular vein and the superior vena cava, removing the implanted hemodialysis catheter, inserting a percutaneous transluminal angioplasty (PTA) catheter into the vascular access path previously occupied by the hemodialysis catheter, the PTA catheter comprising an elongated shaft having an infusion lumen, an expandable dilatation chamber disposed on the elongated shaft, and one or more infusion openings in communication with the infusion lumen positioned proximally adjacent to the expandable dilatation chamber, expanding at least the expandable dilatation chamber to disrupt fibrin sheath material present along the vascular access path, administering a radiographic contrast enhancing agent through the one or more infusion openings, and radiographically imaging the vascular access path and associated fibrin sheath material. The expandable dilatation chamber comprises an inflatable balloon. The method may comprise expanding and contracting the dilatation chamber multiple times while radiographically imaging the vascular access path and the fibrin sheath material. The method may comprise radiographically imaging at least a portion of the jugular vein. Expanding the expandable dilatation chamber may comprise expanding an expandable rigid spacer. The catheter may include a single infusion opening.

In another implementation, a method of visualizing and/or treating a catheterization path for an implanted hemodialysis catheter, comprises selecting a hemodialysis patient in need of an implanted hemodialysis catheter, inserting a percutaneous transluminal angioplasty (PTA) catheter into the jugular vein or subclavian vein and then into the brachiocephalic vein, the PTA catheter comprising an elongated shaft having an infusion lumen, an expandable dilatation chamber disposed on the elongated shaft, and one or more infusion openings in communication with the infusion lumen positioned proximally adjacent to the expandable dilatation chamber, expanding at least the expandable dilatation chamber to open a stenosis in the brachiocephalic vein, administering a radiographic contrast enhancing agent through the one or more infusion openings, and radiographically imaging portions of the jugular vein and/or subclavian vein. The expandable dilatation chamber may comprise an inflatable balloon. Expanding the expandable dilatation chamber may comprise expanding an expandable rigid spacer. The catheter may include a single infusion opening. The method may comprise expanding the dilatation chamber at one or more other stenoses in the venous catheterization path.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-D schematically illustrate side views of an exemplary dilatation balloon catheter representing different stages in dilating a narrowed segment adjacent hemodialysis vascular access and occluding same segment during material perfusions, in accordance with some embodiments of the present invention;

FIGS. 7A-D schematically illustrate different illnesses in vascular accesses treatable by exemplary balloon catheters, in accordance with some embodiments of the present invention;

FIGS. 8A-D schematically illustrate an exemplary balloon catheter having a uniform diameter and cross sections thereof at different locations therealong, in accordance with some embodiments of the present invention;

DESCRIPTION OF EMBODIMENTS OF THE INVENTION

Figure 1A:
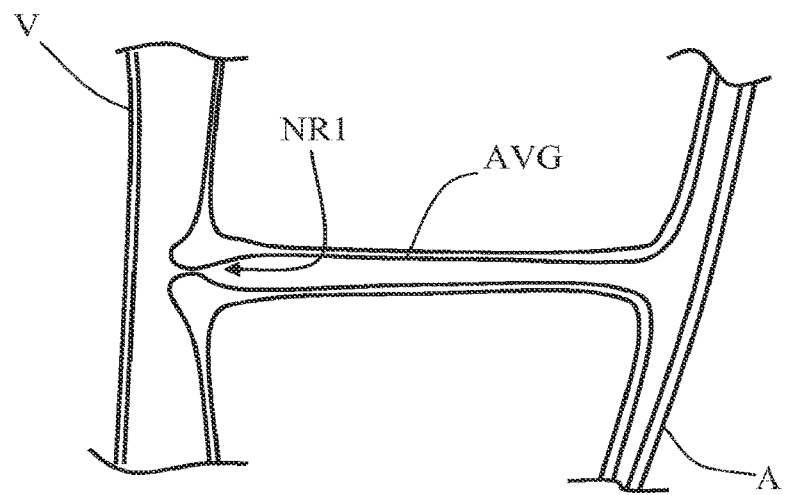
FIGS. 1A-C schematically illustrate side cut views of exemplary narrowed segments adjacent dialysis vascular access, in accordance with an embodiment of the present invention.

The following preferred embodiments may be described in the context of exemplary dilatation and/or recanalization systems and methods in blood vessels, such as dialysis vascular access recanalization or treatment procedures, for ease of description and understanding. However, the invention is not limited to the specifically described devices and methods, and may be adapted to various clinical applications without departing from the overall scope of the invention.

The present invention, in some embodiments thereof, relates to systems and methods for treating narrowed or occluded blood vessels, and in particular to dilatation balloon catheters for dilating occluded or narrowed vein, artery or graft portions such as in dialysis vascular access or at remote locations. In some embodiments of the invention, the dilatation balloon catheters of the present invention are capable and/or configured to exert and maintain enough dilatation pressures such as moderate-to-high pressures over 1 atmospheres or more, optionally 5 atmospheres or more, or ultra-high pressures of 15 atmospheres or more, optionally 25 atmospheres or more. In some embodiments, the dilatation balloon catheters of the present invention are capable and/or configured to remain inflated, optionally at least partly when inflated to chosen pressures, for prolonged continuous periods, optionally 1 minute or more, optionally 3 minutes or more, optionally 10 minutes or more.

In some embodiments of the present invention, at least part of the time while remaining inflated, the balloon catheter is used to disperse a fluid, optionally continuously, into the vascular access (e.g., graft or fistula), optionally an infusion material containing at least one of a contrast enhancing agent, a drug agent (e.g., antimitotic agent) and a flushing fluid (e.g., saline). Optionally, the dilatation balloon at least partly occludes the target blood vessel or graft (e.g., a vascular access) during at least part of the infusion period, thereby lowering the blood flow rate therethrough or completely stops it. Optionally, the infusion material is dispersed via an infusion port provided proximally to, optionally adjacent, the balloon.

Figure 1B:
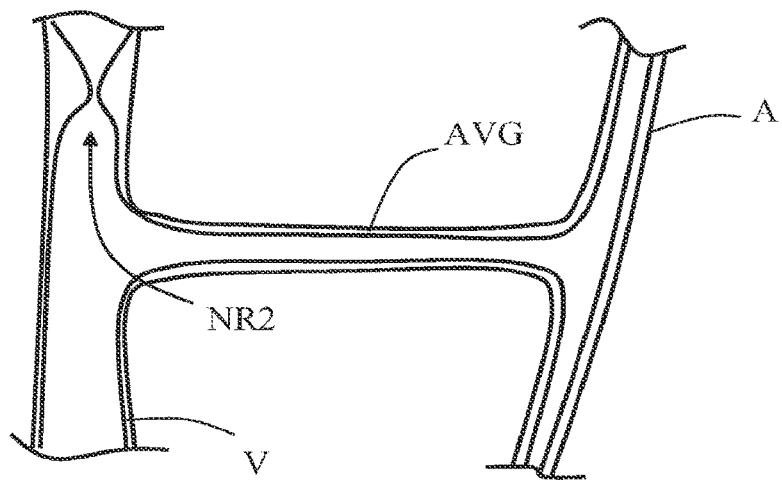
Figure 1C:
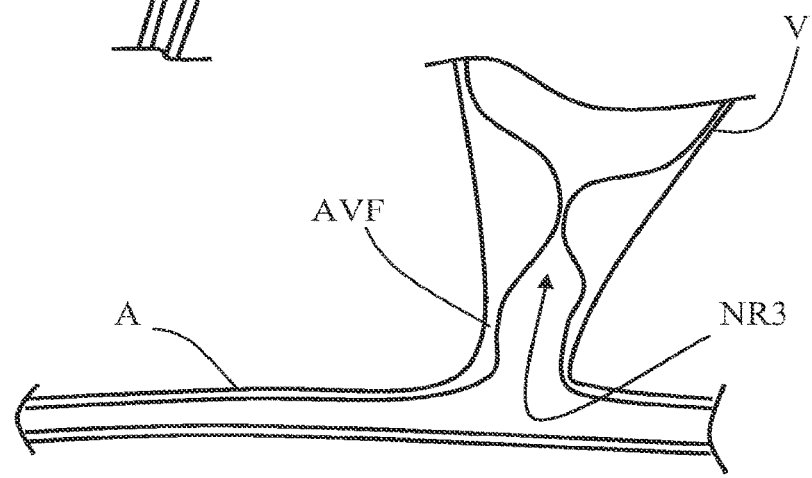

Referring now to the drawings, FIGS. 1A-C schematically illustrate side cut views of exemplary narrowed segments adjacent dialysis vascular access, in accordance with an embodiment of the present invention. FIG. 1A shows a narrowing NR1 at a junction of vein V and an arteriovenous (AV) graft AVG interconnecting vein V and an artery A. FIG. 1B shows a narrowing NR2 located in vein V adjacent its junction with graft AVG. FIG. 1C shows an obstruction or a complete narrowing NR3 located in an arteriovenous fistula AVF adjacent junction of vein V and artery A. Such narrowing or obstructions may be formed of any combination of different factors commonly resulting change of natural blood flow regimes, artifact anastomoses and/or introduction of PTFE or other synthetic or natural grafts.

Dr. Prabir Roy-Chaudhury in "Hemodialysis Vascular Access Dysfunction—Opportunities for Targeting an Unmet Clinical Need" (US Renal Disease, 2006), the disclosure of which is fully incorporated herein by reference, lists several factors. In early fistula failure, often evidenced as a stenotic venous and/or arterial segment very close to the junction, the failure to reach mature fistulas is believed to include a multifactorial etiology as a result of diverse insults including: (a) hemodynamic stressors that predispose to endothelial damage and constriction rather than dilation; (b) vascular injury at the time of surgery, especially as a result of venous tension and/or torque; (c) poor venous and arterial anatomy (vessel size and configuration); (d) previous venipunctures; (e) demographic factors such as race, gender, ethnicity and obesity; and (f) genetic factors that influence the aggressiveness of the response to injury cascade. Late fistula failure and AV graft stenosis begins from venous neointimal hyperplasia (VNH), which results in venous stenosis followed by thrombosis. In the setting of AV grafts this occurs most commonly at the graft-vein anastomosis or in the first 2-3 cm of proximal vein, although stenosis was evidenced at any different points within the entire dialysis access circuit. Alternative mechanisms for vascular stenosis include: vascular remodeling, adventitial migration from the adventitia into the intima and presence of circulating stem cells.

An aspect of some embodiments of the present invention relates to a dilatation balloon catheter comprising an expandable chamber sized and configured to expand a vein lumen portion above a nominal size thereof. Such a balloon may be referred to as an "angioplasty balloon." The vein may be a cephalic vein or a basilic vein. Optionally, the vein is a brachiocephalic vein. The nominal size of the vein lumen portion may be at least 3 mm, optionally at least 6 mm, optionally at least 10 mm, or higher, but it will be appreciated that lumen sizes lower than these values, or at any intermediate value can be treated with the methods and devices described herein. In some embodiments of the invention, the expandable chamber is capable of opening a narrowed and/or obstructed segment and/or recanalizing vessel such as a dialysis vascular access. The vascular access may be an arteriovenous graft or an arteriovenous fistula.

In some embodiments of the invention, the expandable chamber comprises an inflatable balloon. In some embodiments, the inflatable balloon is designed for burst pressures exceeding 1 atmosphere, optionally exceeding 5 atmospheres. In some embodiments, the balloon is a high pressure balloon configured to maintain a non-ruptured form under inflation pressures exceeding 15 atmospheres, optionally exceeding 20 atmospheres, optionally exceeding 30 atmospheres, or higher. In exemplary embodiments, the inflatable balloon is configured to maintain said non-ruptured form under continuous and/or repeated expansions under said inflation pressures for at least 1 minute, optionally for at least 3 minutes, optionally for at least 5 min, optionally for at least 10 minutes, optionally for at least 30 minutes, or higher. Such prolonged durations allow the use of the balloon to occlude, fully or partially, a blood vessel portion, optionally following dilatation of the portion or another portion of the blood vessel, while optionally infusing a fluid (e.g., a contrast medium and/or a medicament) proximally to the balloon. Thus, in some advantageous embodiments, an angioplasty balloon may also be used as an occlusion balloon.

The dilatation balloon catheter includes an inflation lumen interconnecting an inflation inlet port provided at its proximal end and an inflation exit port opened at the space created between the balloon wall and the catheter body segment enclosed by the balloon. In some embodiments, the balloon is inflated using saline, optionally with contrast enhancing material.

In some embodiments, the dilatation balloon catheter further includes an infusion exit port located proximally to the balloon or the expandable chamber for allowing an infusion material to exit the dilatation balloon catheter. In some embodiments, the dilatation balloon catheter comprises an infusion inlet port and an infusion lumen, intercommunicating the infusion inlet port and the infusion exit port.

The infusion inlet port may be connectable to communicate with an interior of an appendix reservoir containing infusion material. In a first exemplary embodiment, the infusion material includes contrast enhancing fluid. In a second exemplary embodiments, the infusion material comprising a medication that includes at least one active agent, for example at least one of a mitotic inhibitor, a antimitotic agent, a mitosis modulator, an antineoplastic agent, an antiproliferative agent, an immunosuppressive agent, paclitaxel, sirolimus, zotarolimus, everolimus, Biolimus A9, an anticoagulation agent and heparin. In a third exemplary embodiment, the infusion material comprising a medication solvent, enhancer and/or facilitator, for example a material, compound or agent that includes at least one of an antiproleferative agent solvent, Cremophor EL, castor oil, ethanol, albumin, protamine sulfate, an antiproliferative agent enhancer, antibiotics and vitamin.

The infusion inlet port may be, optionally, alternatively or additionally, connectable to a source for continuously flowable flushing fluid. Saline, with or without a contrast enhancing fluid, with or without medication, or any additive or enhancer of some sort, may be injected to flush any residual clot material from the vessel.

Optionally, alternatively or additionally, the dilatation balloon catheter further comprises a dedicated medication dispersion lumen for allowing a medication to pass therethrough and exit through a medication exit port, which may be located adjacent to the infusion exit port, optionally distally, optionally proximally, optionally juxtaposing or optionally circumferentially distant thereto.

In some embodiments of the invention, the dilatation balloon catheter comprises a guidewire lumen for allowing a guidewire to pass therethrough and exit through a guidewire exit port located distally to the infusion exit port. In some embodiments, the guidewire exit port is located at the balloon catheter tip, distal to the balloon. Optionally, the infusion lumen is also a guide wire lumen so it is configured such that both a guidewire and infusion fluids are passable therethrough according to need. In some embodiments, such a multifunctional lumen includes at least one inlet port or optionally two inlet ports for insertion of fluids and guidewire, and at least two exit ports—a proximal exit port provided proximally to balloon for dispersion of infusion fluids, and a distal exit port provided distal to the balloon, meant for guidewire passage. Optionally, fluids are injected only when guidewire is absent or alternatively when guidewire is at least partially enclosed in the infusion lumen. Optionally at least one valving mechanism is provided in the infusion lumen so that fluids are selectively set to disperse only from the proximal exit port and not from the distal exit port. Balloon catheters comprising a combined infusion-guidewire lumen, a proximal infusion exit port and valving mechanism are described in U.S. provisional application No. 61/752,649, the disclosure of which is fully incorporated herein by reference.

Reference is now made to FIGS. 2A-D which schematically illustrate side views of exemplary dilatation balloon catheters 100, 150, 200 and 250, respectively, in accordance with an embodiment of the present invention.

Figure 2A:
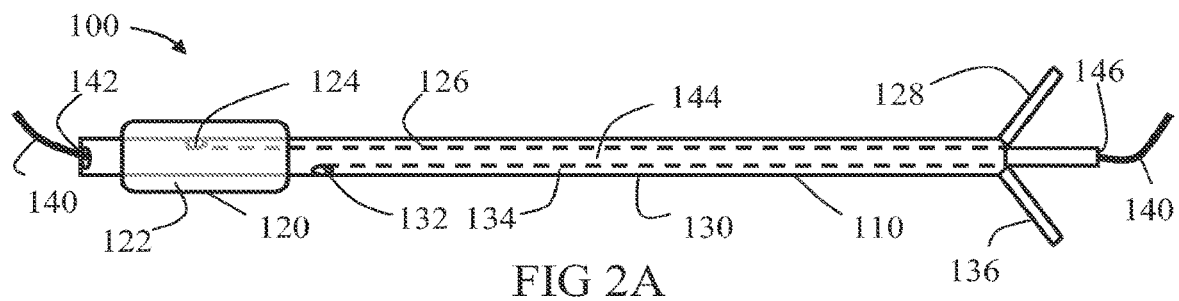
FIGS. 2A-D schematically illustrate side views of exemplary dilatation balloon catheters, in accordance with an embodiment of the present invention.

In FIG. 2A, dilatation balloon catheter 100 includes an elongate shaft 110 connectable at its distal end with a balloon 120. Shaft 110 may be made from a biocompatible polymer, rigid or semi-rigid, as known to art. Balloon 120 may be an occlusion balloon type and/or a dilatation balloon type; and may include a compliant, a semi-compliant, a non-compliant, or an ultra-non-compliant wall (for example, comprising a non-compliant polymeric layer impregnated with non-stretchable strengthening fibers, such as Kevlar). In many advantageous embodiments, balloon 120 is configured so that it can function effectively as both a dilatation balloon and an occlusion balloon. In some cases, as described above, this may be accomplished by having the balloon material and inflation properties satisfy a Shaft 110 includes an inflation lumen 126 provided along a length thereof, interconnecting an inlet inflation port 128, located at a proximal end thereof, and an inflation exit port 124 provided at balloon 120 interior 122. Balloon 120 may be inflatable by pressurizing inflation medium to its interior through inflation exit port 124. Inflation medium may include saline or oil, with or without contrast enhancing materials.

Shaft 110 also includes infusion means 130 including an infusion lumen 134 interconnecting an infusion inlet port 136, located at a proximal end thereof, and an infusion exit port 132 located distally to infusion inlet port 136 but proximal and adjacent to balloon 120. The advantage of positioning the infusion exit port proximally to the balloon, in case that the balloon serves to occlude unwanted directional passage, is that the infusion material may be directed proximally to the balloon thereby improving efficiency and safety of the procedure, optionally allowing visualization and/or preventing clot formation in the conduit. After properly occluding the vein portion, contrast material and/or thrombolytic drugs may be safely injected prior to restoration of flow thereby preventing concerns relating to the migration of clots into the arterial system. In some embodiments (not shown), infusion lumen 134 is opened at more than one infusion exit ports located adjacent or proximal to infusion exit port 132 but in any event proximal to balloon 120. Optionally and alternatively (not shown), infusion exit port 132 is positioned distally to balloon 120 thereby allowing flow of infusion material only distally and away from balloon 120.

Dilatation balloon catheter 100 includes a guidewire 140 provided in guidewire lumen 144 extending in and along shaft 110 and interconnecting proximal guidewire entry 146 and distal guidewire opening 142. Dilatation balloon catheter 110 may be an over-the-wire (OTW) type catheter or a rapid-exchange (Rx) type catheter.

In some embodiments of the invention, dilatation balloon catheter 100 may be used for percutaneous transluminal angioplasty (PTA), for example for dilating and/or recanalizing narrowed portion NR1 shown in FIG. 1A, narrowed portion NR2 shown in FIG. 1B and/or obstructed or fully narrowed portion NR3 shown in FIG. 1C. Optionally, balloon 120 is inflatable to high pressures capable of opening narrowing in stenotic cephalic or basilica veins, optionally to 15 atmospheres or higher, optionally to 20 atmospheres or higher. Optionally and additionally, balloon 120 may be pressurized to at least partially take the form of an entire cross section along a lumen section to thereby occlude the lumen section and prevent flow of infusion material to pass therethrough. In some embodiments, balloon 120 includes a compliant or a semi-compliant portion and in same or other embodiments, balloon 120 includes a non-compliant or an ultra-non-compliant portion.

In some embodiments, a dilatation balloon catheter according to aspects of the present invention includes an expandable chamber which comprises a compliant layer expandable to take a form constrained by surrounding boundaries of the vein lumen portion, optionally readily expanded above said nominal size, and to occlude the lumen portion from a contrast enhancing fluid passing between periphery thereof and the surrounding boundaries. Optionally, additionally or alternatively, the expandable chamber comprises a non-compliant layer expandable to form the vein lumen portion to an expanded size above a nominal size having predefined boundaries.

In some embodiments of the invention, the dilatation balloon catheter includes a first independently inflatable balloon having a compliant layer and a second independently inflatable balloon having a non-compliant layer. Optionally, the expandable chamber comprises the second independently inflatable balloon and is positioned proximally distanced to the first independently inflatable balloon. Optionally and alternatively, the expandable chamber comprises the second independently inflatable balloon and is disposed within the first independently inflatable balloon.

Figure 2B:
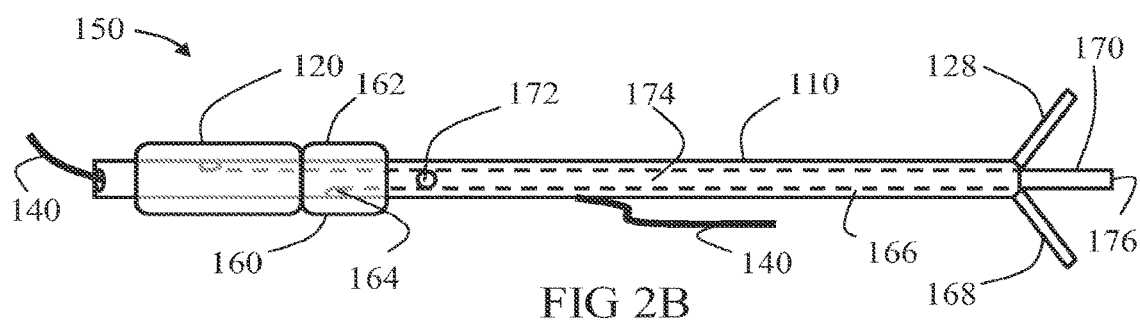

In FIG. 2B, dilatation balloon catheter 150 includes a similar design of catheter 100 comprising elongated shaft 110, dilatation balloon 120 provided at distal end thereof and communicating with inflation inlet port 128, and guidewire 140 provided along a dedicated lumen extending partially along shaft 110 length. Vein occlusion means 160 is provided separately to dilatation balloon 120 and comprising an occlusion balloon 162 positioned adjacently proximally to dilatation balloon 120. Occlusion balloon 162 is inflatable by introduction of inflation medium (e.g., saline) through an inflation exit lumen 164 communicating with its interior. Inflation exit port 164 is interconnected via an inflation lumen 166 to an inflation inlet port 168 located at a proximal end of shaft 110. An infusion exit port 172 is provided adjacent and proximal to occlusion balloon 162 and is interconnected via an infusion lumen 174 to an infusion inlet port 176 located at the proximal end of shaft 110.

In some embodiments, balloon 120 includes a non-compliant or an ultra-non-compliant layer and is capable of being inflated without rupture or yielding under pressures exceeding 15 atmospheres. Such pressures may be maintained or be occasionally repeated for prolonged durations, for example of 1 minute or more, or even up to 30 minutes or even more than 30 minutes, in which prolonged dilatations are made for improved yielding and reforming of the narrowed vein segment to an expanded form and/or infusion material (e.g., contrast media, flushing fluid and/or medication) is continuously injected in directionally allowed path in the vein and/or vascular access lumen for improved efficacy. In some embodiments, occlusion balloon 162 includes a compliant or a semi-compliant layer and is designed for inflation pressures of less than 15 atmospheres, optionally less than 10 atmospheres, optionally less than 5 atmospheres, optionally about 1 atmosphere or less. In some embodiments, dilatation balloon 120 is configured to maintain high pressures for 1 to 3 minutes periods, or higher, or lower, whereas occlusion balloon 162 is configured to maintain lower pressures for 1 to 30 minutes, or higher, or lower.

Figure 2C:
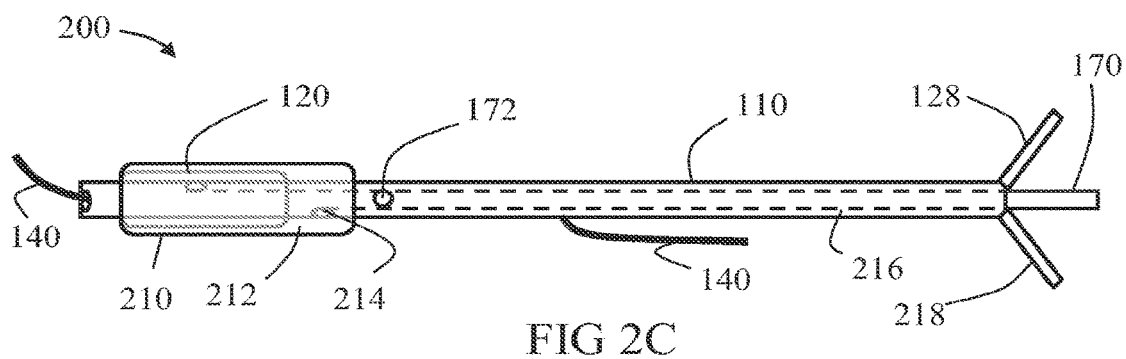

In FIG. 2C, dilatation balloon catheter 200 includes a similar design of catheters 100 or 150, comprising elongated shaft 110, dilatation balloon 120 provided at distal end thereof and communicating with inflation inlet port 128, and guidewire 140 provided along a dedicated lumen extending partially along shaft 110 length. Vein occlusion means 210 is provided over dilatation balloon 120 and comprising an occlusion balloon 212 sized and positioned to enclose or encapsulate dilatation balloon 120. Occlusion balloon 212 is inflatable by introduction of inflation medium (e.g., saline) through an inflation exit lumen 214 communicating with its interior. Inflation exit port 214 is interconnected via an inflation lumen 216 to an inflation inlet port 218 located at a proximal end of shaft 110. Infusion exit port 172 is now provided adjacent and proximal to occlusion balloon 212 on shaft 110.

In some embodiments, dilatation balloon 120 includes a non-compliant or an ultra-non-compliant layer and is capable of being inflated without rupture or yielding under pressures exceeding 15 atmospheres. In some embodiments, occlusion balloon 212 includes a compliant or a semi-compliant layer and is designed for inflation pressures of less than 15 atmospheres, optionally less than 10 atmospheres, optionally less than 5 atmospheres, optionally about 1 atmosphere or less. In some embodiments, dilatation balloon 120 is configured to maintain high pressures for 1 to 3 minutes periods, or higher, or lower, whereas occlusion balloon 212 is configured to maintain lower pressures for 1 to 30 minutes, or higher, or lower. In some embodiments, dilatation balloon 120 is configured to inflate at high pressures when the covering occlusion balloon 212 is deflated, though compliant enough to take the form of the inflated dilatation balloon 120. In some embodiments, occlusion balloon 212 is configured to inflate to occlude and take a form of a vein lumen portion when dilatation balloon 120 is deflated and/or at least partially inflated.

Figure 2D:
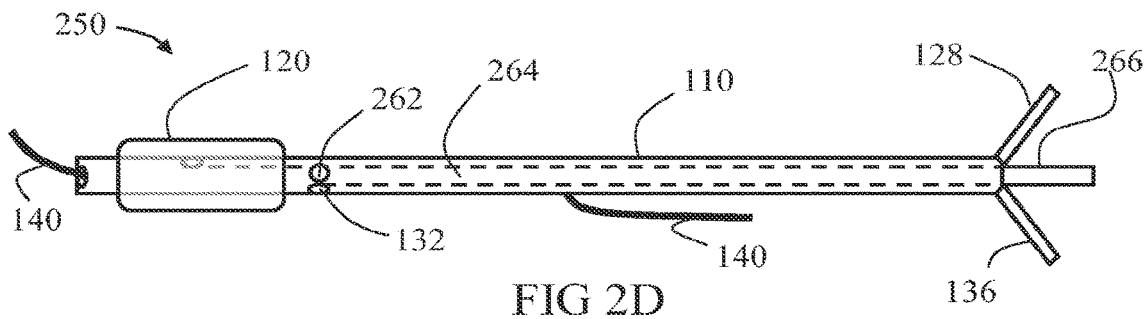

In FIG. 2D, dilatation balloon catheter 250 includes a similar design of catheter 100, comprising elongated shaft 110, dilatation balloon 120 provided at distal end thereof and communicating with inflation inlet port 128, and guidewire 140 provided along a dedicated lumen extending partially along shaft 110 length. A separate medication dispersion exit port 262 is provided adjacent infusion exit port 132 adjacent and proximal to balloon 120. Medication dispersion exit port 262 is interconnected via a medication dispersion lumen 264 to a medication inlet port 266 located at a proximal end of shaft 110. This way, medication may be dispersed in vein lumen while other infusion materials are injected or withheld, according to need, via infusion exit port 132. In sequence or in parallel, or in any combination thereof, contrast media, medication, other active agents, active agent enhancers or facilitators, flushing fluids, or other flowable materials, may be dispersed via exit ports 132 and/or 262.

In some embodiments of the present invention, a dilatation balloon catheter is coated or impregnated, at least partially, with at least one of mitotic inhibitor, antimitotic agent, mitosis modulator, antineoplastic agent, antiproliferative agent, immunosuppressive agent, paclitaxel, sirolimus, zotarolimus, everolimus, Biolimus A9, anticoagulation agent, and heparin.

In some embodiments, additionally or alternatively to previous shown embodiments, the expandable chamber comprises an expandable rigid spacer, wherein a compliant layer is disposed between the spacer and the surrounding boundaries. In some embodiments, the spacer comprises a self-expandable member provided in covering sheath. Optionally, the self-expandable member is radially expandable when the covering sheath is proximally withdrawn. Optionally and alternatively, the spacer comprises a selectively expandable cage member. Optionally and alternatively, the spacer comprises a braid selectively compressible from a first length indicative of a smaller spacer diameter to a second length indicative of a greater spacer diameter. Optionally, alternatively or additionally, the spacer comprises a shape memory material and is shapeable from a first slender shape at less than body temperature to a second expanded shape at body temperature.

Figure 3A:
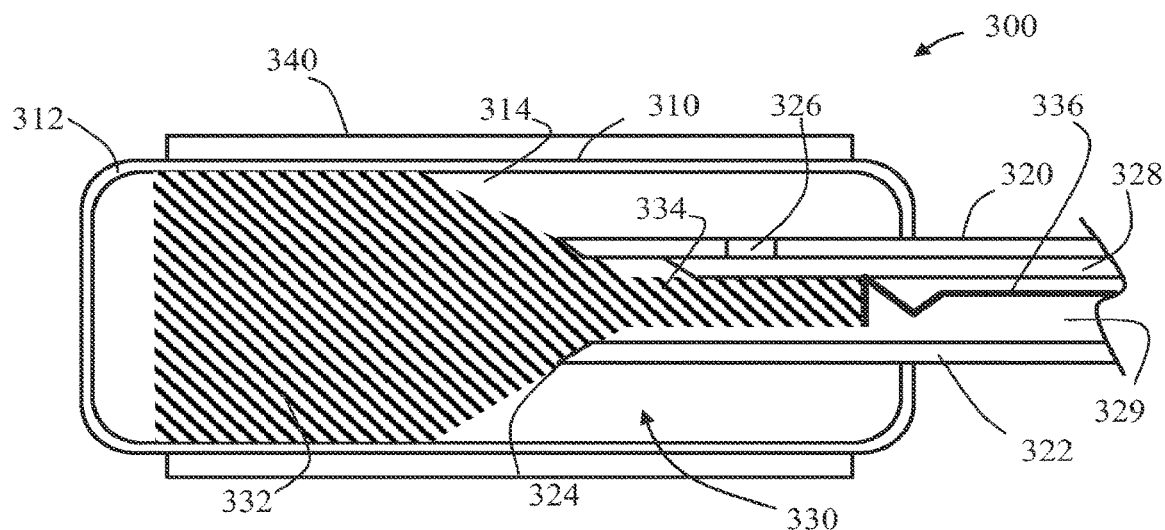
FIGS. 3A-B schematically illustrate side cut views showing distal portions of exemplary occlusion balloon catheters comprising exemplary expandable spacers, in accordance with some embodiments of the present invention.
Figure 3B:
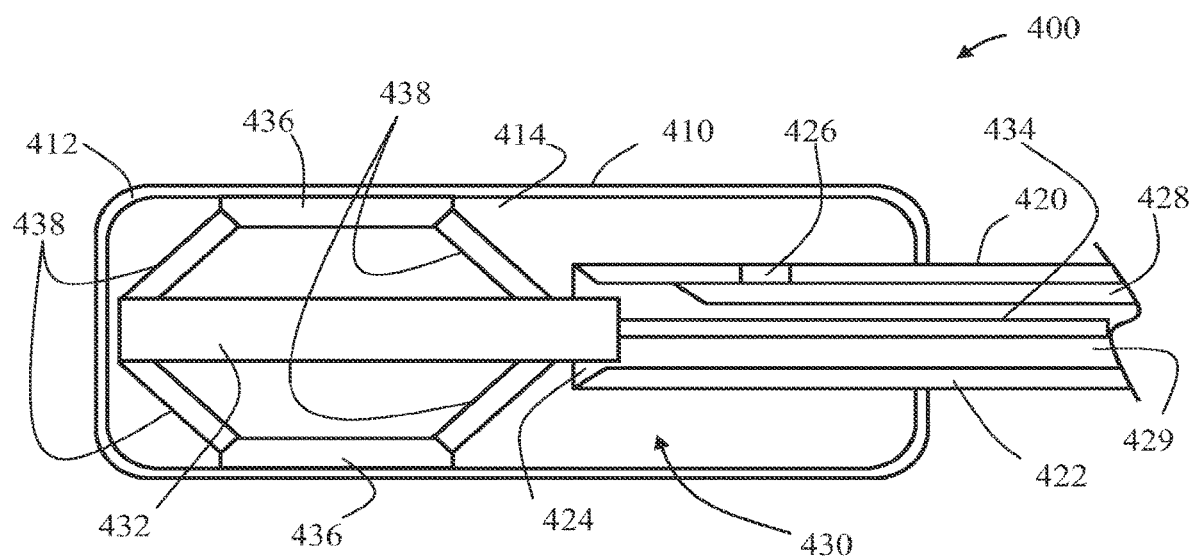

Reference is now made to FIGS. 3A-B which schematically illustrate side cut views showing distal portions of exemplary occlusion balloon catheters 300 and 400, respectively, comprising exemplary expandable spacers, 330 and 430, respectively, in accordance with some embodiments of the present invention.

In FIG. 3A, occlusion balloon catheter 300 includes a balloon 310 having a compliant layer 312 enclosing an interior 314. In some embodiments, balloon 310 is a drug eluting balloon (DEB), coated with drug layer 340, and is especially fitted and configured to treat and/or prevent, at least partially, stenosis and/or restenosis in veins, optionally specifically in cephalic and/or basilic veins. In some embodiments, drug layer 340 includes an antiproliferative agent, such as a solid form or powdered paclitaxel. Occlusion balloon catheter 300 includes a hollow shaft 320 comprising a rigid, semi-rigid or elastic wall 322 enclosing an inflation lumen 328 and a spacer actuation lumen 329. Hollow shaft 320 at its distal end is protruding in interior 314 of balloon 310 such that inflation exit port 326 and spacer actuation opening 324 is fixedly positioned therein. A self-expandable spacer 330 is selectively deployable to self-expand in interior 314 or extractable to a smaller collapsed form when pulled into spacer actuation lumen 329. Shown in FIG. 3A an intermediate stage where a distal portion 332 of self-expandable spacer 330 is protruding out of lumen 329 through opening 324 to expand in interior 314, while a proximal portion 334 is kept in collapsed form in lumen 329. Relative positioning of self-expandable spacer 330 in spacer actuation lumen 329 is applicable with rod 336 connected to proximal end of spacer 330 and is configured to push or pull spacer 330 in lumen 329 as appropriate.

In some embodiments, balloon 310 is a compliant balloon sized and configured to allow occlusion of a lumen in a cephalic or a basilic vein portion while infusion material and/or medication and/or flushing medium is dispersed in the vein lumen, while preventing flowing of such materials distally across balloon 310. In some embodiments, balloon 310 is not configured to inflate at high pressures to apply PTA expansive forces, thus incapable of dilating a narrowed or an obstructed vein portion, adjacent a hemodialysis vascular access. Such dilatation is applicable by releasing self-expandable spacer 330, at least partially, to an expanded form being equal or greater than a nominal size of vein lumen. In some embodiments, when expanding, spacer 330 exerts forces having magnitudes high enough to dilate the narrowed or obstructed portion. Self-expandable spacer 330 may be kept continuously released as needed, for example for periods of 1 minute or more, and may be extracted or released as needed.

In FIG. 3B, occlusion balloon catheter 400 includes a balloon 410 having a compliant layer 412 enclosing an interior 414. In some embodiments, balloon 410 is especially fitted and configured for PTA procedures in cephalic and/or basilic veins. Occlusion balloon catheter 400 includes a hollow shaft 420 comprising a rigid, semi-rigid or elastic wall 422 enclosing an inflation lumen 428 and a spacer actuation lumen 429. Hollow shaft 420 at its distal end is protruding in interior 414 of balloon 410 such that inflation exit port 426 and spacer actuation opening 424 is fixedly positioned therein. A selectively expandable cage 430 is selectively deployable to expand or contract, as chosen, in interior 414. Shown in FIG. 3B fully deployed stage where cage 430 is fully expanded. Cage 430 comprises a core member 432, a plurality of pressing members 436 that are hingedly connected to actuation members 438 interconnecting them to core member 432. Actuation of cage 430 is applicable with rod 434 connected to proximal end of core member 432. A jackscrew mechanism (not shown) is embedded in core member 432 such that clockwise rotation of rod 434 will force cage 430 to expand up to its maximal expanded size, whereas a counterclockwise rotation of rod 434 will collapse cage 430 up to a fully collapsed form (not shown).

In some embodiments, balloon 410 is a compliant balloon sized and configured to allow occlusion of a lumen in a cephalic or a basilic vein portion while infusion material and/or medication and/or flushing medium is dispersed in the vein lumen, while preventing flowing of such materials distally across balloon 410. In some embodiments, balloon 410 is not configured to inflate at high pressures to apply PTA expansive forces, thus incapable of dilating a narrowed or an obstructed vein portion, adjacent a hemodialysis vascular access. Such dilatation is applicable by forcing cage 430 to expand, selectively, to a chosen size, being equal or greater than a nominal size of vein lumen. In some embodiments, when expanding, cage 430 exerts forces having magnitudes high enough to dilate the narrowed or obstructed portion. Cage 430 may be kept continuously expanded as needed, for example for periods of 1 minute or more, and may be collapsed and expanded as needed. If a drug coated balloon or drug impregnated balloon in dialysis access needs to be inflated for prolonged periods to time to reach better effectiveness the proximal infusion port can be used for intermittent or confusion infusion of fluid to prevent clot formation during the prolonged treatment.

Also, if a mode of drug delivery to the stenosed segment includes infusion of the drug directly into the stenosed segment through a porous or fenestrated balloon and the drug being infused over a prolonged period of time into the diseased segment, then the proximal infusion port can be used to maintain access patency during the procedure.

In an aspect of some other embodiments of the present invention, there is provided a method for recanalizing a hemodialysis vascular access, optionally in a narrowed, obstructed or otherwise stenotic portion in a basilica or cephalic vein portion. In some embodiments, the method comprising at least one of the following steps, not specifically in such order:

inserting a dilatation balloon catheter in a narrowed vein lumen portion adjacent a dialysis vascular access through an opening in the dialysis vascular access;

positioning the expandable chamber appositionally to the lumen portion;

expanding the expandable chamber to expand the lumen portion to above its nominal size;

applying the dilatation balloon catheter to occlude the expanded lumen portion; and administering contrast enhancing fluid through the infusion exit port.

In some embodiments, the step of applying the dilatation balloon to occlude the lumen portion is comprised in the step of expanding the expandable chamber to expand the lumen portion. Optionally, such applying and/or expanding comprises inflating a first independently inflatable balloon. Optionally, such inflating includes elevating a pressure in the first independently inflatable balloon to a maximal pressure being at least 15 atmospheres. Optionally, such a maximal pressure is maintained and/or repeatedly obtained for at least 1 minute. Optionally and alternatively, after a dilatation of a narrowed vessel portion, the balloon is used to occlude same or other vessel portion in substantially lower pressures as were applied during the dilatation. In some embodiments, the first independently inflatable balloon is coated or impregnated with a first anti-restenosis medication.

Optionally and alternatively, the applying comprises expanding an expandable rigid spacer.

Optionally, alternatively or additionally, the method further includes the step of delivering a second anti-restenosis medication through the infusion exit port.

In some embodiments, the first anti-restenosis medication and/or the second anti-restenosis medication comprises at least one of a mitotic inhibitor, an antimitotic agent, a mitosis modulator, an antineoplastic agent, an antiproliferative agent, an immunosuppressive agent, paclitaxel, sirolimus, zotarolimus, everolimus, Biolimus A9, an anticoagulation agent, and heparin.

In some embodiments, the method further includes the step of flushing the narrowed vein lumen portion with a continuous stream of flushing fluid through said infusion exit port.

Reference is now made to FIGS. 4A-D which schematically illustrate side views of dilatation balloon catheter 100 representing different stages in dilating a narrowed segment NR of vein V adjacent hemodialysis vascular access and occluding same segment during material perfusions, in accordance with some embodiments of the present invention. As shown in FIG. 4A, catheter 100 is provided towards narrowed segment NR over guidewire 140 until balloon 120 is nested therein. As chosen, and as shown in FIG. 4B, balloon 120 is inflated to dilate narrowed segment NR to over its nominal size. Balloon 120 is optionally a high pressure and/or non-compliant balloon, optionally strengthened with reinforcing fibers, such as aramid or para-aramid synthetic fibers (e.g., Kevlar™, made by Du-Pont™), although other fibers or wires types (e.g., dyneema, twaron, nylon, vectran or others) or other strengthening means or designs (e.g., wall thickening) may be used. Balloon 120 may be maintained in a chosen expanded shape for prolonged periods, for example 1 minute or more, optionally 3 minutes or more, optionally 5 minutes or more, optionally 10 minutes or more.

In some embodiments, balloon 120 is configured to occlude, at least partly, the now expanded narrowed segment NR for travel of fluids therethrough. As shown in FIG. 4C, contrast medium 510 is then injected via infusion exit port 132 and is allowed to travel in vein V lumen only proximally and away from balloon 120. Medication 520 or any enhancers or facilitators for medication may then be dispersed (as shown in FIG. 4D) via infusion exit port 132 and, based on its physical properties (e.g., viscosity and/or relative specific gravity) may be kept adjacent narrowed segment NR for prolonged periods, optionally over 5 minutes, optionally over 10 minutes.

Figure 5:
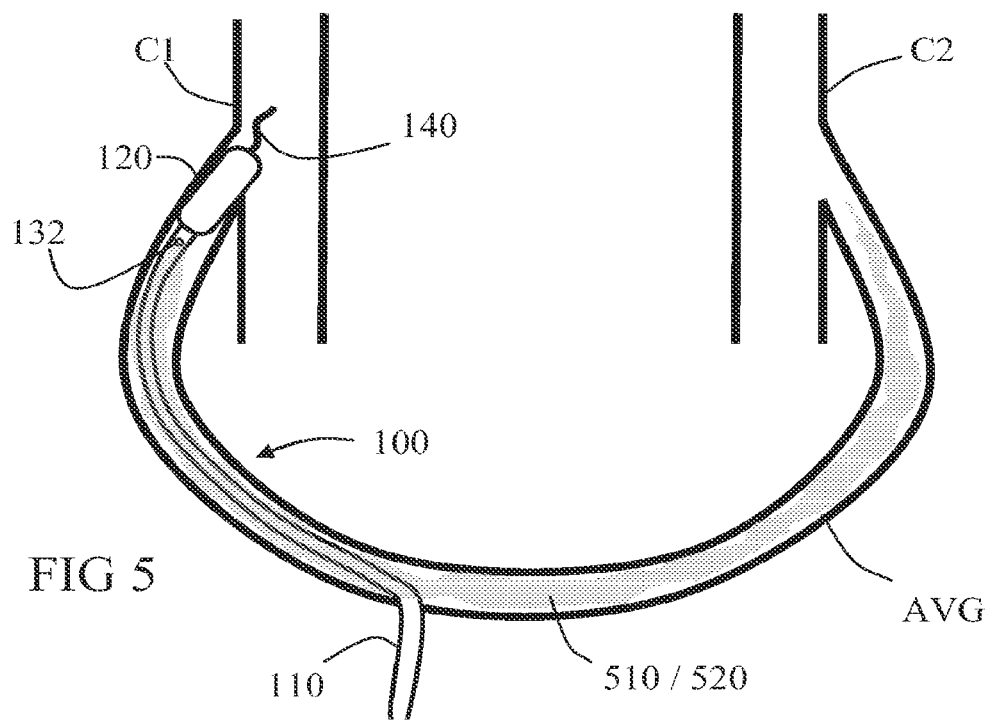
FIG. 5 schematically illustrate top cut views of an exemplary balloon catheter deployed to occlude an anastomosed portion between a conduit and a graft while dispersing a fluid along graft length, in accordance with some embodiments of the present invention.

Reference is now made to FIG. 5 which schematically illustrate top cut views of balloon catheter 100 when deployed to occlude an anastomosed portion between a conduit C1 and a graft AVG, connecting conduit C1 and a conduit C2, while dispersing a fluid along graft AVG length, in accordance with some embodiments of the present invention. In a first embodiment, conduit C1 is a vein and conduit C2 is an artery. In some embodiments, balloon 120 is shown inflated following a dilatation procedure to expand a local narrowing, in which it was dilated to maximal pressures of 15 atmospheres or more, optionally 25 atmospheres or more. Optionally and alternatively, balloon 120 was not used previously to dilate a narrowed portion. As shown, balloon 120 is shown expanded to decrease or totally stop the blood flow rate therethrough traveling upstream from conduit C2 (e.g., artery) to conduit C1 (e.g., vein). In some embodiments, balloon 120 is kept inflated for at least 3 minutes, optionally at least 10 minutes, optionally at least 20 minutes or even more. During inflation time, infusion material is dispersed through infusion exit port 132. Optionally, alternatively or additionally, same or other infusion material is dispersed via a fenestrated wall portion in balloon 120 (not shown). Dispersion material may include contrast medium 510 and/or medication 520. In this example, contrast medium 510 and/or medication 520 travels along graft AVG length in a reversed direction to that of a normal blood flow passing in the graft in order to allow visualization and/or treat the graft and/or anastomosis areas. Optionally, alternatively or additionally, same or other medication than medication 520 is coating balloon 120 exterior. In some embodiments, balloon 120 is gradually unpressured from ultra high pressures during infusion period, optionally until reaching 5 atmospheres or less, optionally 1 atmosphere or less.

In some embodiments, same or similar treatment can be performed in a fistula at an arteriovenous anastomosis area.

Optionally and alternatively, conduit C1 is an artery and conduit C2 is a vein, and balloon 120 is shown occluding, fully or partially, an arterial anastomosis area for treating most of all of graft AVG with medication 520. In this example, balloon 120 is not or is not used for dilatation in order to avoid mechanical damage to the arterial anastomosis and adjacent tissues.

Optionally, alternatively or additionally, balloon 120 is repeatedly used to dilate graft AVG at different portions along its length, while, optionally, medication 520 is dispersed, continuously or in between each dilatations.

In some embodiments, balloon 120 is introduced into graft AVG and travels therein until deployment when in a compressed form, in which its outer diameter is same or smaller than outer diameter of shaft 110.

Figure 6A:
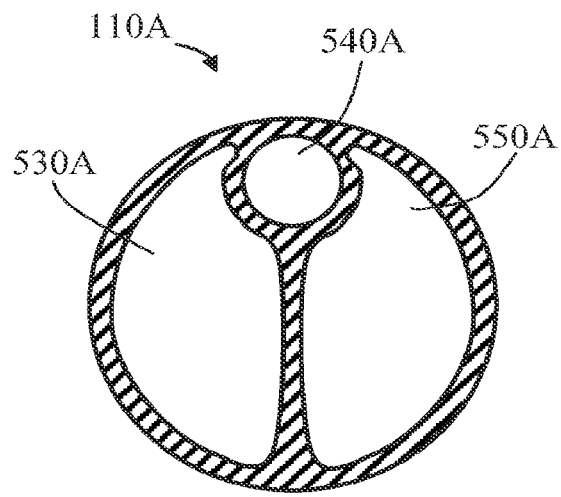
FIGS. 6A-B schematically illustrate cross sectional cut views of two dilatation balloon catheters, in accordance with some embodiments of the present invention.
Figure 6B:
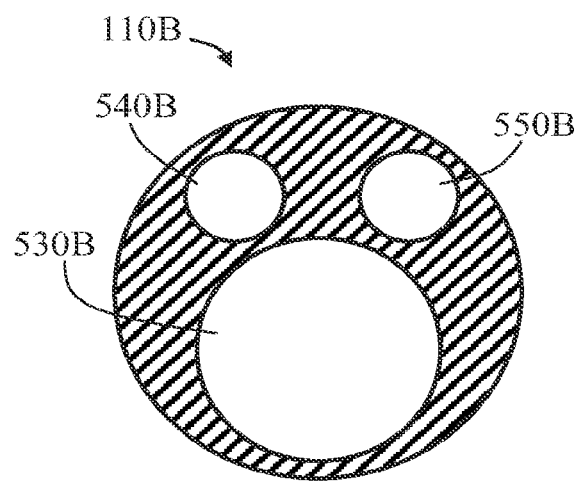

Reference is now made to FIGS. 6A-B which schematically illustrate cross sectional cut views of two dilatation balloon catheters, 100A and 100B, respectively, in accordance with some embodiments of the present invention. Catheter 100A is shown with a shaft 110A having a small guidewire lumen 540A and two large inflation lumen 530A and infusion lumen 550A and catheter 100B is shown with a shaft 110B having a large inflation lumen 530B and two small guidewire lumen 540B and infusion lumen 550B. Guidewire lumens 540A and 540B are of standard size allowing passing therethrough of commercially available guidewires, such as those having diameters between 0.015 and 0.025 inch. A large inflation lumen, as in lumens 530A and 530B, is needed for rapid inflation and deflation of balloon 120 being formed and configured to maintain a non-ruptured form under pressures exceeding 25 atmospheres or more during prolonged periods of 1 minute or more. A large infusion lumen, such as lumen 550A, is needed in case of viscous contrast medium or medication and/or when high flow rates are needed, for example for flushing. In some embodiments large lumens 530A, 550A and/or 530B are 0.03 inch or more in diameter, optionally 0.05 inch or more, optionally 0.1 inch or more, optionally 0.5 inch or more. In some embodiments of the invention, infusion lumens 550A and/or 550B respectively communicates with infusion inlet ports (not shown), each is further connectable to a source for continuously flowable flushing fluid.

Reference is made to FIGS. 7A-D which schematically illustrate different illnesses in vascular accesses treatable by exemplary balloon catheters, in accordance with some embodiments. In FIG. 7A, a fistula type vascular access is shown in which a vein is connected to an artery at an arteriovenous anastomosis AVA. A narrowing NR is present in vein portion adjacent anastomosis AVA. Passage 610 shows introduction and travel route of an exemplary balloon catheter according to the present invention (for example, balloon catheter 100) for treating narrowing NR and recanalizing the shown vascular access. In some embodiments, balloon catheter 100 is used to perform angioplasty procedure with some advantages originating from aspects of the present invention. Optionally balloon 120 is non-compliant. The procedure includes at least one of the following steps (not necessarily in same order):

1. Inserting balloon catheter 100 into the vein, optionally through a vascular sheath, optionally over a guide wire (not shown) and advancing it towards anastomosis AVA, generally along passage 610, optionally guided under fluoroscopy, until reaching narrowing NR;
2. performing angioplasty by dilating balloon 120 according to need;
3. while the balloon is being inflated and/or is maintained inflated (thereby optionally functioning as an occlusion balloon), injecting contrast enhancing material via infusion exit port 132 into the fistula, optionally allowing the contrast media to flow towards the heart so that other possible narrowed portions may be traced adjacent AVA or upstream;
4. deflating balloon 120 so blood can flow again through AVA clearing the contrast enhancing material;
5. advancing balloon catheter 100, optionally approximately 4 to 5 cm beyond AVA into the artery, then injecting contrast enhancing material once more to image the treated area of anastomosis AVA and analyzing current condition and deciding if further sessions are needed;
6. removing balloon catheter 100 and any other instrumentation (such as guidewire and/or sheath).

In FIG. 7B, a fistula type vascular access is shown in which a vein is connected to an artery at an arteriovenous anastomosis AVA. A narrowing NR is present in vein portion upstream and away from anastomosis AVA. Passage 620 shows introduction and travel route of an exemplary balloon catheter according to the present invention (for example, balloon catheter 100) for treating narrowing NR and recanalizing the shown vascular access. In some embodiments, balloon catheter 100 is used to perform angioplasty procedure with some advantages originating from aspects of the present invention. Optionally balloon 120 is non-compliant. The procedure includes at least one of the following steps (not necessarily in same order):

1. inserting balloon catheter 100 into the vein, optionally through a vascular sheath, optionally over a guide wire (not shown) and advancing it away from anastomosis AVA, generally along passage 620, optionally guided under fluoroscopy, until reaching a position proximal to or adjacent narrowing NR;
2. injecting contrast enhancing material via infusion exit port 132 in order to locater and/or observe narrowing NR;
3. advancing balloon catheter 100 further until reaching narrowing NR;
4. performing angioplasty by dilating balloon 120 according to need;
5. while the balloon is being inflated and/or is maintained inflated (thereby optionally functioning as an occlusion balloon), injecting contrast enhancing material via infusion exit port 132 into the fistula, towards anastomosis AVA and into the artery;
6. deflating balloon 120 so blood can flow again through AVA clearing the contrast enhancing material;
7. injecting contrast enhancing material once more to image the treated area, analyzing current condition and deciding if further sessions are needed;
8. removing balloon catheter 100 and any other instrumentation (such as guidewire and/or sheath).

In some embodiments, similar procedure can be performed to a narrowed graft using some or all steps as described above.

In FIG. 7C, a fistula type vascular access is shown in which a vein is connected to an artery at an arteriovenous anastomosis AVA. A narrowing NR is present in vein portion adjacent anastomosis AVA. Clotting substance CL is present in the vein and blocks flow passage therethrough. Passage 630 shows introduction and travel route of an exemplary balloon catheter according to the present invention (for example, balloon catheter 100) for clearing clotting substance CL and recanalizing the shown vascular access. In some embodiments, balloon catheter 100 is used to perform declotting procedure with some advantages originating from aspects of the present invention. Optionally balloon 120 is non-compliant. The procedure includes at least one of the following steps (not necessarily in same order):

1. inserting balloon catheter 100 into the vein, optionally through a vascular sheath, optionally over a guide wire (not shown) and advancing it toward anastomosis AVA, generally along passage 630, optionally guided under fluoroscopy, until reaching anastomosis AVA;
2. inflating balloon 120 at junction in order to prevent clots from entering the artery;

3. while the balloon is being inflated and/or is maintained inflated (thereby optionally functioning as an occlusion balloon), injecting contrast enhancing material via infusion exit port 132 into the fistula;
4. imaging (taking angiogram) the vein to locate blocked and narrowed areas (with clots CL and/or narrowing NR);
5. injecting clot dissolving material via an opening proximal to balloon 120 (optionally via infusion exit port 132 or another dedicated medicament exit port) until clots CL dissolve and disengage from vein walls;
6. still while the balloon is being inflated and/or is maintained inflated (thereby optionally functioning as an occlusion balloon), injecting again contrast enhancing material via infusion exit port 132 into the fistula;
7. deflating balloon 120 so blood can flow again through AVA clearing dissolved clots CL and the contrast enhancing material;
8. removing balloon catheter 100 and any other instrumentation (such as guidewire and/or sheath).

In FIG. 7D, a graft type vascular access is shown connecting a vein to an artery. Clotting substance CL is present in the graft and blocks flow passage therethrough. Passages 640 and 650 show consecutive introduction and travel route of an exemplary balloon catheter according to the present invention (for example, balloon catheter 100 with a compliant occlusion type balloon) for clearing clotting substance CL and recanalizing the shown vascular access. In some embodiments, balloon catheter 100 is used to perform declotting procedure with some advantages originating from aspects of the present invention. The procedure includes at least one of the following steps (not necessarily in same order):

1. inserting an occlusion type balloon catheter 100 into the vein or in graft AVG adjacent vein, optionally through a vascular sheath, optionally over a guide wire (not shown) and advancing it away from the venous anastomosis, generally along passage 640, optionally guided under fluoroscopy, until reaching the arterial anastomosis;
2. inflating balloon 120 in order to prevent clots from entering the artery;
3. while the balloon is being inflated and/or is maintained inflated, injecting contrast enhancing material via infusion exit port 132 into graft AVG;
4. imaging (taking angiogram) graft AVG to locate blocked areas (with clots CL);
5. injecting clot dissolving material via an opening proximal to balloon 120 (optionally via infusion exit port 132 or another dedicated medicament exit port) until clots CL dissolve and disengage from vein walls;
6. pulling back the inflated balloon 120 to possibly dislodge an arterial plug;
7. deflating balloon 120 and injecting contrast enhancing material via infusion exit port 132 into the graft;
8. removing balloon catheter 100 and any other instrumentation (such as guidewire and/or sheath);
9. optionally repeating at least one of steps 1-8 in an opposite route, such as generally along passage 650.

In some embodiments, balloon catheters according to the present invention are deployed (inserted and progressed in the vasculature) without use of a sheath (a "sheathless procedure").

In some embodiments, a balloon dilatation catheter according to the present invention includes three lumens passing at least partially therealong and has a substantially uniform diameter with the dilatation balloon outer diameter being substantially equal or smaller than the outer diameter of the catheter body, when it is the collapsed formation, for example during travel in the cardiovascular vessels and before deployment. In some embodiments, only the distal portion of the balloon catheter, distally to the dilatation balloon, is substantially smaller in diameter, optionally including a single lumen, optionally a lumen intended for passing a guidewire therethrough. Optionally and additionally, when the balloon collapses after deflation, it regains outer diameter being equal or smaller than that of the catheter shaft. Maintaining such small dimension throughout balloon dilatation catheter length allows the use of smaller introducer sheathes.

FIGS. 8A-D schematically illustrate an exemplary balloon catheter 1000 having a uniform diameter, and cross sections thereof at different locations therealong. Balloon catheter 1000 may be similar or identical to catheter 100 in at least one of size, balloon type and infusion port location, or may be a variation thereof. Catheter 1000 includes an elongated body 1100 having a length and at least three portions with different cross sections and different outer diameters as shown in FIGS. 8B-D. In its distal end, elongated body is covered, partially, with a dilatation balloon 1200. In some embodiments, balloon 1200 is collapsed and maintained folded, optionally rolled, over a dedicated recessed portion of elongated body 1100. In an optional design (not shown), an outer sheath holds balloon 1200 tightly in its rolled/collapsed formation until inflation, optionally the outer sheath bursts and/or discarded, optionally in a dedicated cabinet in elongated body 1100.

In its proximal portion, being the longest, elongated body 1100 includes a cross section as shown in FIG. 8B, defining an infusion lumen 1310, a balloon inflation lumen 1320 and a guidewire lumen 1330. Infusion lumen 1310 may be sized and configured such to allow medically approved flow rates of at least one of contrast enhancing flowaable material, flowable medication and/or flushing liquid (e.g., saline). Balloon inflation lumen 1320 may be sized and configured such to allow rapid and continuous inflation of dilatation balloon 1200. Guidewire lumen 1330 may be sized and configured such to allow passing therethrough and/or riding over wires being 0.01 to 0.03 inch in diameter, optionally 0.015 to 0.025 inch in diameter. All three lumens travel along the entire length of the proximal segment and originating with thee dedicated inlet ports, namely: infusion inlet port 1110, balloon inflation inlet port 1120 and guidewire inlet port 1130. In this exemplary embodiment, guidewire lumen 1330 is relatively small and is located at the center of the proximal portion of catheter body 1100, while infusion lumen 1310 and inflation lumen 1320 are substantially greater in size in order to allow high flow rates of both infusion and inflation media. Infusion lumen ends at the premises of an infusion exit port 1140.

Next to its distal end portion, elongated body 1100 is reduced in size to allow integration with balloon 1200 which gradually adds to its outer boundaries, when in collapsed form, an overall diameter being substantially the same or slightly smaller than the outer diameter of the proximal portion of elongated body 1100. A 2nd cross section of elongated body 1100, illustrated in FIG. 8C, shows its size reduction when reduced to two lumens, namely, guidewire lumen 1330 and balloon inflation lumen 1320. Balloon inflation lumen 1320 ends with inflation exit port 1150 positioned inside balloon 1200. A 3rd cross section of elongated body 1100, illustrated in FIG. 8D, shows a further reduction in diameter, now only slightly larger than guidewire lumen 1330. Still, balloon 1200 at its compacted/ rolled state adds diameter to reach an overall outer diameter substantially same or smaller than that of elongated body 1100 at its proximal portion, as described above. Optionally, elongated body 1100 further extends distally away from balloon 1200, so that catheter 1000 end portion is substantially smaller in diameter. At the distal tip of elongated body 1100, there is located an opening 1160 of guidewire lumen 1330 through which a guidewire (not shown) may outwardly extend.

In some occasions, minimization of catheter's lumens cross-sections is advantageous. In one example, there may be a need for a small diameter catheter for intraluminal passage (e.g., 3 F to 5 F) so it is more complex to introduce three lumens. In a second example, there may be a need to fortify the catheter shaft for high pressure dilatations (as in vascular access recanalization in certain anatomies), so it may be advantageous to decrease overall lumens size in a certain shaft diameter. In some embodiments, a dilatation balloon catheter according to the present disclosure includes a single lumen which is used, at least in part, both for fluids transfer and dispersion ("infusion") as well as for guidewire passage.

Figure 9A:
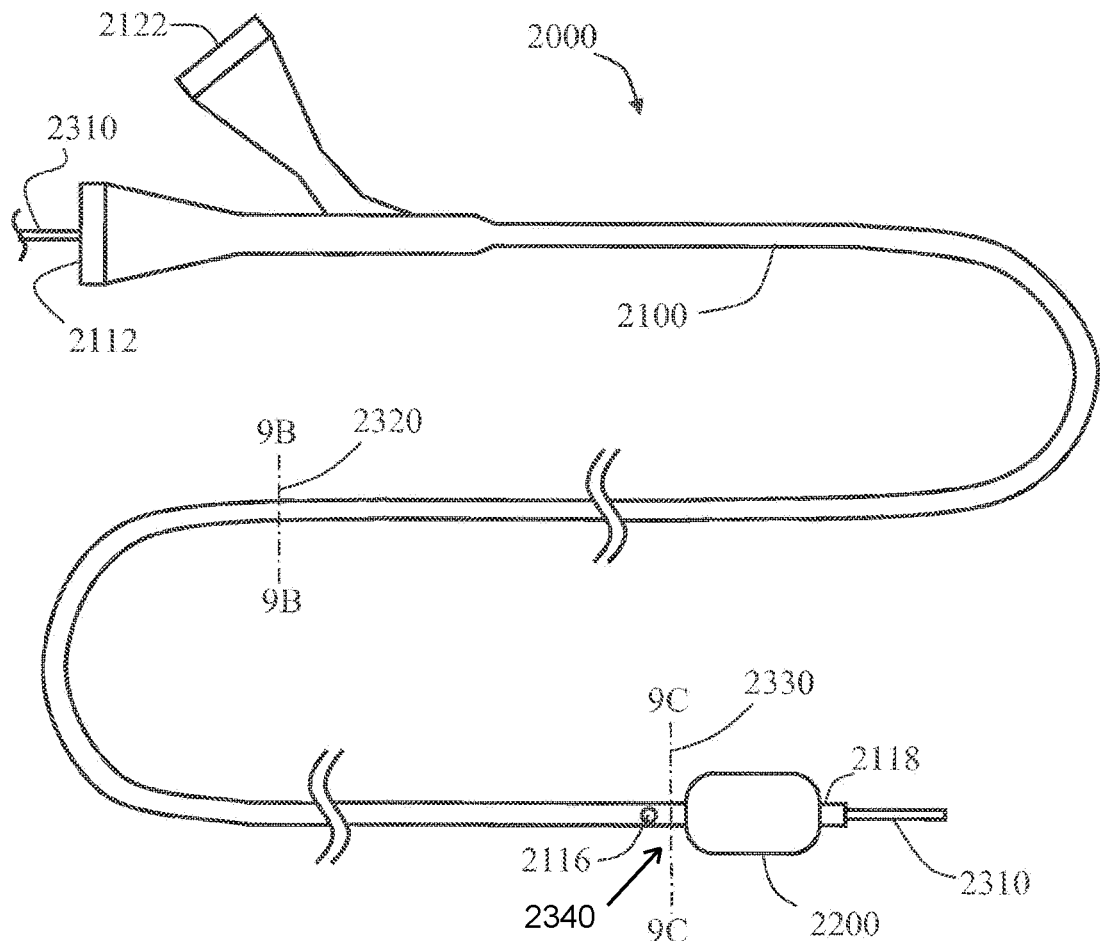
FIGS. 9A-C schematically illustrate an exemplary balloon catheter comprising a combined infusion-guidewire lumen, in accordance with embodiments of the present invention.
Figure 9B:
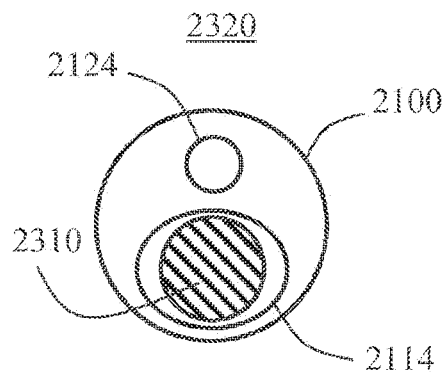
Figure 9C:
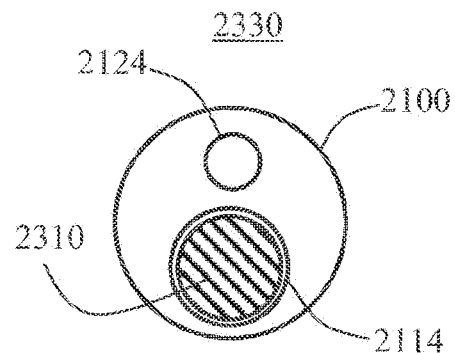

Reference is made to FIGS. 9A-C which schematically illustrate an exemplary dilatation balloon catheter 2000 comprising a combined infusion-guidewire lumen (referred to as infusion lumen 2114) with an optional selective valving mechanism 1300. Catheter 2000 includes a shaft 2100 having, a length, a proximal end and a distal end, and a wall enclosing infusion lumen 2114 which is extending along shaft's 2100 length and opened at both proximal and distal ends with corresponding proximal opening 2112 and distal opening 2118. Infusion lumen 2114 is further opened with a lateral infusion opening 2116 disposed in shaft's 2100 wall between the proximal end and the distal end.

An inflatable member 2200 is connected to shaft 2100 adjacent its distal end, distal to lateral infusion opening 2116. An inflation lumen 2124, sealed to infusion lumen 2114, extends between a proximal inflation opening 2122, at shaft's 2100 proximal end, and a distal inflation port 2126, opened to an interior of inflatable member 2200. Inflatable member 2200 may be a compliant balloon, a semi-compliant balloon or a non-compliant balloon.

A valving mechanism according to the present disclosure may be any type of controller, such as a mechanical device, for selectively controlling a flow parameter of a fluid, for example a flow rate. A valving mechanism may be set between two or more modes, including a fully closed mode in which flow is substantially absent, and a fully opened valve in which fluid is allowed to travel in maximal velocity. According to some preferred embodiments of the present disclosure, a valving mechanism includes an elongated member such as a wire (e.g., a guide wire) operational to selectively pass through or withdraw from an infusion lumen portion sized and shaped substantially the same as external boundaries of a correlating portion thereof, such that when upon occupying the infusion lumen portion then substantially or completely no flow will pass therethrough, while when it is fully withdrawn from the infusion lumen portion, fluid passage can be feasible. An optional valving mechanism may be provided in infusion lumen 2114 distal to lateral infusion opening 2116. Valving mechanism may be selectively operable to block distal opening 2118 of infusion lumen 2114 such that fluid passing distally through infusion lumen 2114 shall exit mainly or solely through lateral infusion opening 2116 rather than through distal opening 2118. In case that the valving mechanism is set not block distal opening 2118, more flow may pass via distal opening 2118.

As shown, infusion lumen 2114 defines a first segment 2320, extending between proximal opening 2112 and a boundary 2340 adjacent lateral infusion opening 2116, and a second segment 2330, extending between boundary 2340 and distal opening 2118. In some embodiments, first segment 2320 has a first minimal cross section area and second segment 2330 has a second minimal cross section area smaller than the first minimal cross section of first segment 2320. Valving mechanism may include an elongated member, preferably a guide wire 2310 selectively disposable in the first and second minimal cross sections. Guidewire 2310 is preferably sized and configured to pass through proximal opening 2112, infusion lumen 2114 and distal opening 2118, and therefore allow an over-the-wire delivery of catheter 1000 thereupon.

In some embodiments, the second minimal cross section is sized and shaped such that guide wire 2310 can be selectively fit, snugly, in the second minimal cross section in order to achieve blocking of distal opening 2118 and/or second segment 1330 distal to lateral infusion opening 2116. In some embodiments, the second minimal cross section is circular whereas the first minimal cross section is sized and shaped to virtually enclose a circle with identical dimensions to said second minimal cross section (as shown in the shape difference of infusion lumen 2114 in FIG. 9B vs. FIG. 9C). The first minimal cross section may be circular, elliptic or crescent shaped.

A dilatation balloon catheter, such as balloon catheters 100, 1000 or 2000, can also be used to treat stenotic vein portions being substantially remote from site of anastomosis and/or dialysis access, or at occasions where hemodialysis is absent. A common scenario, for example when a vascular access is needed immediately or if AV fistulae or AV shaft implementations are not feasible, includes the introduction of a venous catheter for dialysis via a large vein, usually one of the internal jugular veins. Venous catheters are used either temporarily (usually for durations of weeks to months until a permanent access develops) or permanently (usually lasts for a few months and up to a year), and the dialysis path, from catheter entry point to the superior vena cave, is prone to continuous stenoses. Therefore the need to verify open path for catheterization and maintain such a path opened for prolonged periods in an effective way that will include immediate opening of stenotic portions as well as an immediate follow up visualization with minimal use of contrast media.

A dilatation balloon catheter for creating and/or visualizing a path for dialysis venous catheterization may include a high pressure balloon as previously described (e.g., dilating under pressures of 15 atmospheres or more) or alternatively may include a moderate pressure balloon (e.g., dilating under 10 atmospheres or less), or a regular pressure balloon (e.g., dilating under 5 atmospheres or less).

The following steps, at least in part, may be performed for venous catheterization using exemplary balloon catheter according to the present disclosure (not necessarily in same order):

1. inserting a dilatation type balloon catheter into a large vein, optionally internal jugular vein, optionally through a vascular sheath, optionally over a guide wire and advancing it, optionally guided under fluoroscopy, until reaching the blocked or narrowed site in the central vein, optionally the brachiocephalic vein;

2. inflating the balloon member of the catheter to dilate the narrowed site (angioplasty);
3. while the balloon is being inflated and/or is maintained inflated, injecting contrast enhancing material via the proximal infusion exit port of the balloon catheter so it may flow in the jugular and/or superior vena cava and/or other neck veins;
4. imaging (taking angiogram) veins to locate stenoses and/or blocked areas;
5. if needed, placing a stent in a vein portion, optionally excluding neck veins for extending potential use as central venous access in the future;
6. deflating the balloon member;
7. injecting contrast enhancing material once more to image the treated area, analyzing current condition and deciding if further sessions are needed;
8. removing the balloon catheter and any other instrumentation (such as guidewire and/or sheath).

Figure 10A:
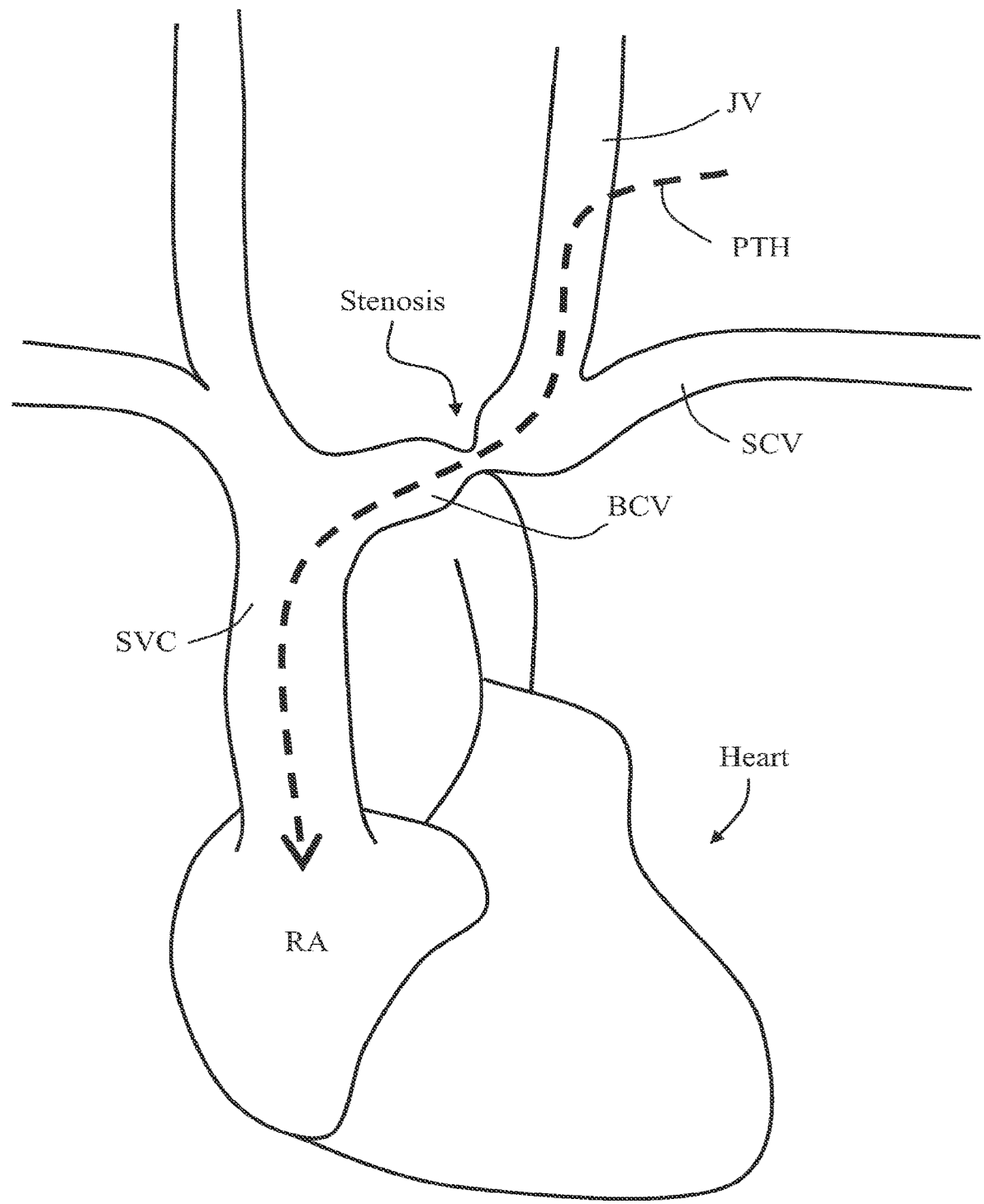
FIGS. 10A-C schematically illustrate stages in a method for dilating a narrowed brachiocephalic vein portion and improving visualization in an internal jugular vein, in accordance with some embodiments of the present invention.
Figure 10B:
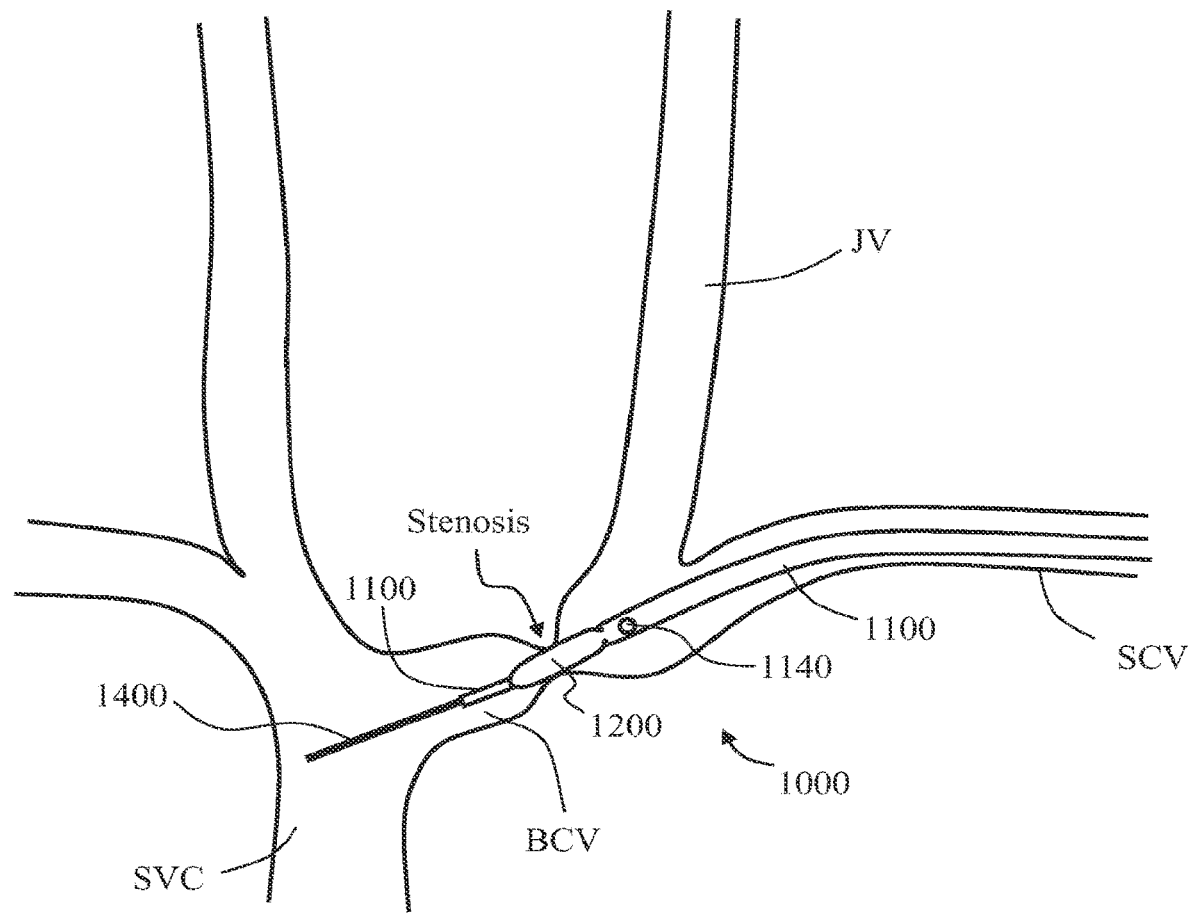
Figure 10C:
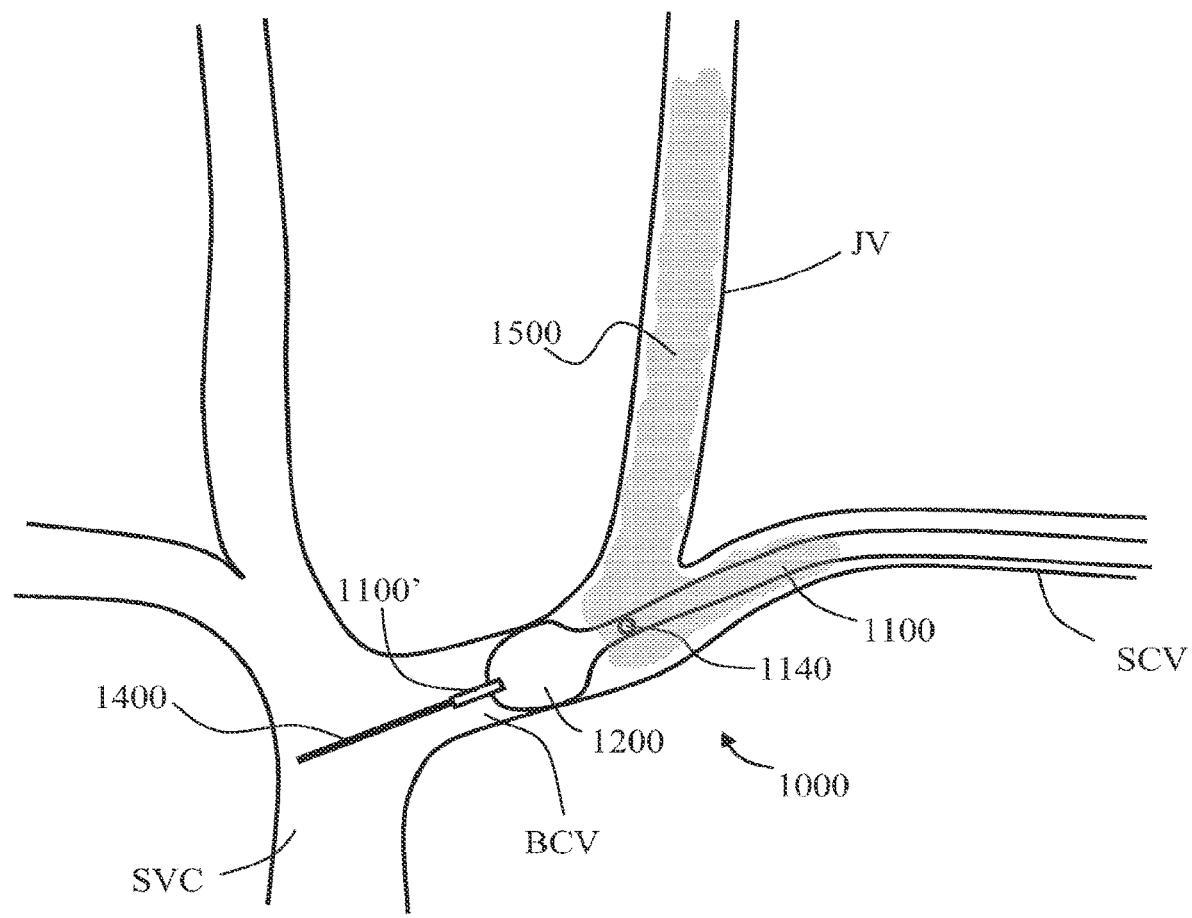

Reference is made to FIGS. 10A-C which schematically illustrate stages in a method for creating a venous catheterization path by first dilating a narrowed brachiocephalic vein portion BCV and then performing an immediate follow up visualization in an internal jugular vein JV. As shown in FIG. 10A, each brachiocephalic vein BCV is formed by the union of internal jugular vein JV and subclavian vein SCV, and the brachiocephalic veins are then joined to form the superior vena cave SVC which extends down to the right atrium RA of the heart. A common practice is to create a catheterization path, such as path PTH shown in FIG. 10A, that begins at an entry point in internal jugular vein JV (although other entry points may be used, such as in the subclavian, the axillary vein or the femoral vein), followed into brachiocephalic vein BCV and optionally further into the superior vena cava SVC and right atrium RA. As in the case of the exemplary illustrated restenosis, common stenoses occur at the brachiocephalic vein BCV, although angioplasty may be needed at other locations along a potential path.

As shown in FIG. 10B, exemplary balloon dilatation catheter 1000 (shown for demonstrative purposes and can be replaced with catheter 100 or catheter 2000, for example) is introduced and extended through the subclavian vein SCV such that balloon 1200 is situated substantially in the stenosis and infusion exit port 1140 is located in or adjacent the JV-SCV junction. Balloon catheter 1000 is optionally deployable in an over-the-wire approach along a previously introduced guidewire 1400 which is extendable from guidewire opening 1160 at the distal tip of elongated catheter body 1100 along guidewire lumen 1330 and out through guidewire inlet port 1130 (not shown). Once in position, dilatation balloon 1200 may be inflated, optionally at moderate to high pressures, by pressurizing inflation media (e.g., saline) via inflation inlet port 1120. After angioplasty, as illustrated in FIG. 10C, contrast medium is infused via infusion exit port 1140 towards jugular vein JV and subclavian vein SCV. At infusion, balloon 1200 may remain at least partially inflated or fully inflated substantially in the dilatation pressure.

Due to local anatomy and physiology of the JV-SCV junction and of the two veins, substantial amount or even most of the contrast medium will flow into jugular vein JV, hence relatively small volumes of contrast medium 1500 are needed for accurate local imaging of the jugular vein JV in a way that may dramatically reduce radiation time and potential of renal damage due to contrast agents. Using imaging, the practicing physician can visualize the effective length of jugular vein JV and entire catheterization path PTH, and may determine if and where is necessary to place stents for facilitating openings at areas prone to narrowing and restenosis.

Optionally, additionally or alternatively, other venous portions of catheterization path PTH are treated with angioplasty using balloon 1200 instead or in addition to the brachiocephalic vein, and/or other portions along path PTH can be chosen for occlusion during contrast medium 1500 infusion, for example the superior vena cava SVC or even upwards the natural blood stream direction.

Optionally, additionally or alternatively, medications are also delivered locally (not shown) using dilatation balloon catheter 1000, either drug eluting from outer surfaces of balloon 1200 and/or flowable medications that are infused, optionally, via infusion exit port 1140 with or without contrast medium 1500.

In an aspect of some embodiments, a dilatation balloon catheter according to the present disclosure is used for fibrin sheath balloon disruption procedures. Fibrin sheath is an inherent process happening with long term implanted dialysis catheters. It is a thin but strong tissue surrounding the catheter and preventing it from proper functioning. Common treatments of fibrin sheath include stripping, thrombolysis, and balloon disruption. With balloon disruption, the catheter is removed a special purpose dilatation balloon catheter is inserted and inflated such that the fibrin sheath is disrupted. Current known dedicated balloon disruption catheters and methods are considered inefficient for imaging the fibrin sheath during and after disruption.

Figure 11A:
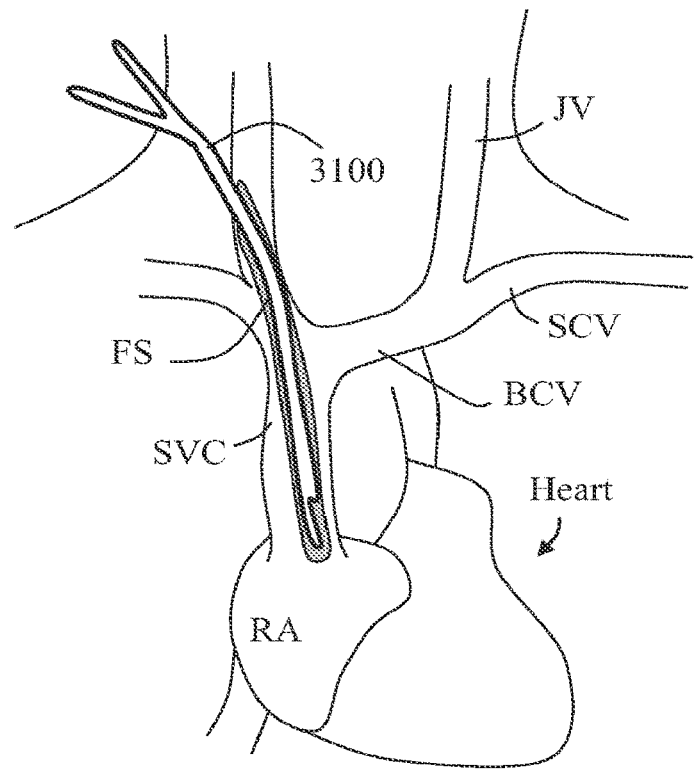
FIGS. 11A-F schematically illustrate stages in a method for fibrin sheath disruption, in accordance with some embodiments of the present invention.

Reference is now made to FIGS. 11A-F which schematically illustrate stages in a method for fibrin sheath disruption, in accordance with some embodiments of the present invention. FIG. 11A shows an exemplary scenario of a first chronic dialysis catheter 3100 having its tip positioned in the superior vena cave SVC and fully surrounded with a fibrin sheath FS as a consequence of prolonged implantation. In some embodiments, an exemplary dilatation balloon catheter 3300 (shown for demonstrative purposes and can be replaced with catheter 100, catheter 1000 or catheter 2000, for example, or be a dedicated variation thereof), comprising an elongated body 3310 enclosing at least two lumens capable of passing therethrough a guidewire, an infusion fluid and a balloon inflation fluid. Balloon catheter 3300 also includes a dilatation balloon member 3320 and an infusion port 3330 located proximally to balloon member 3320. A guidewire inlet port 3340 allows insertion of a guidewire through balloon catheter 3300 for over-the-wire delivering technique. Optionally, balloon member 3320 is inflatable to 8-10 mm, or higher or lower, optionally is a high pressure balloon.

Figure 11B:
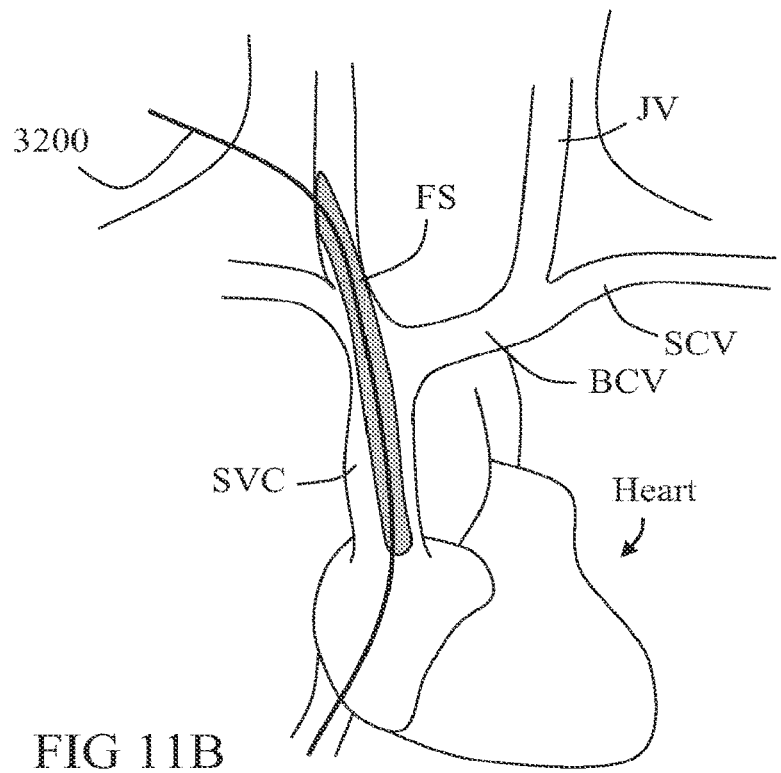
Figure 11C:
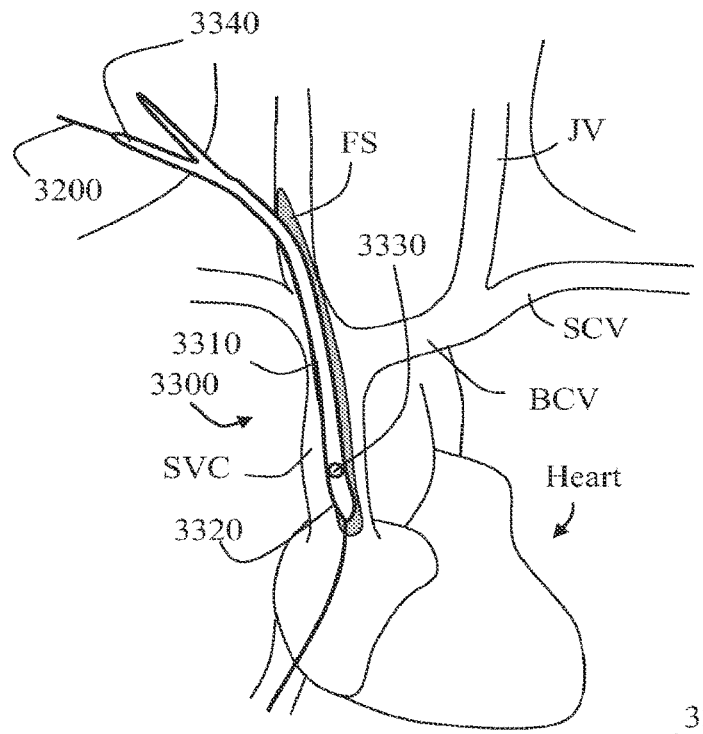
Figure 11D:
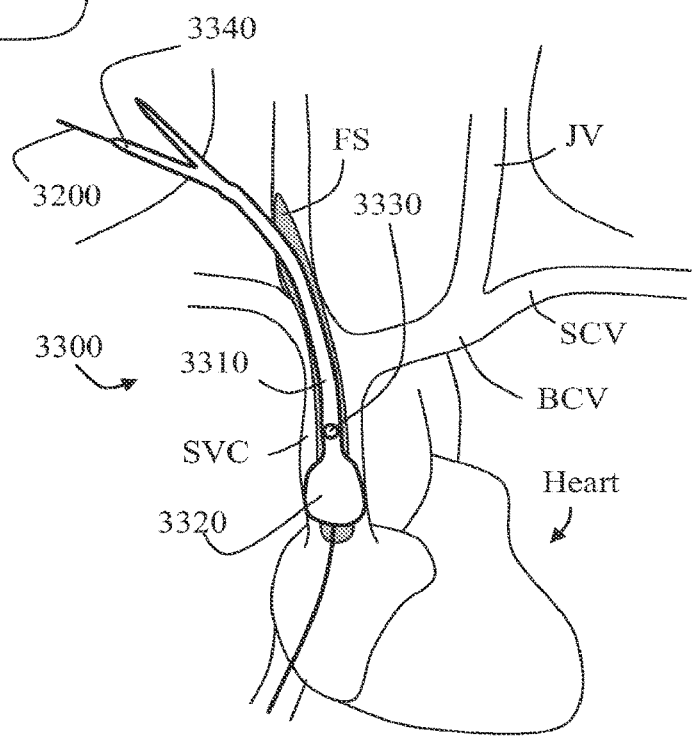
Figure 11E:
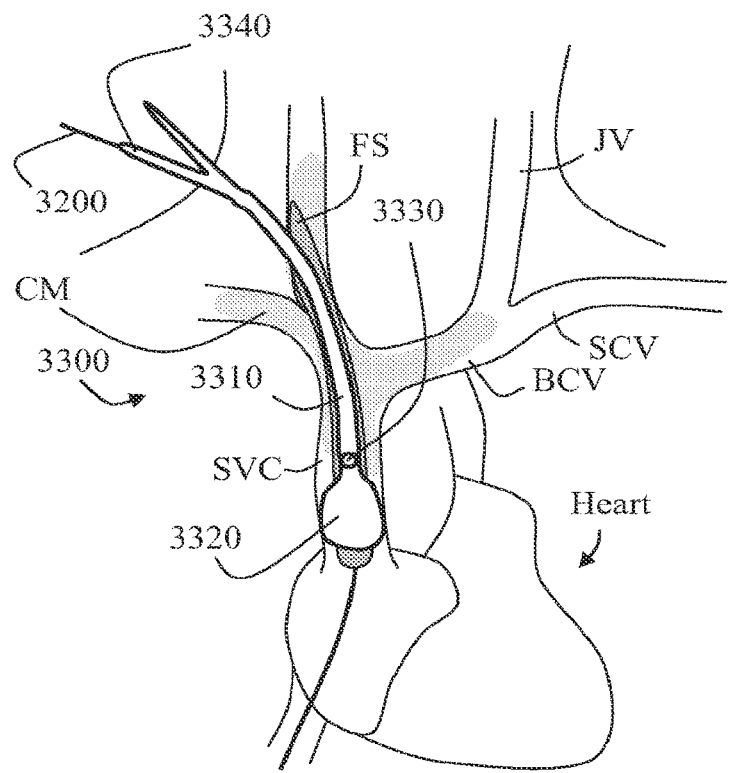
Figure 11F:
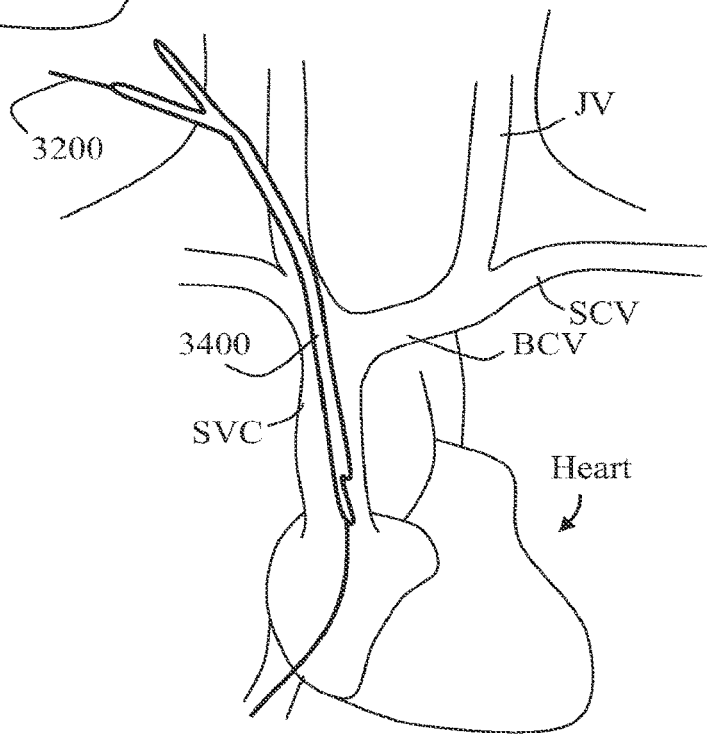

As shown in FIG. 11B, the first dialysis catheter 3100 is removed over a guidewire 3200 and in FIG. 11C dilatation balloon catheter 3300 is introduced over same guidewire 3200 until positioning balloon member 3320 adjacent a target location such as the distal end of the fibrin sheath FS. As shown in FIG. 11D balloon member 3320 is inflated within the fibrin sheath for disrupting it. Then (FIG. 11E), contrast enhancing material CM is injected through infusion port 3330 into the fibrin sheath for enabling visualization of remaining sheath and for performing of additional angioplasty if needed. Thrombolytic agents may also be dispersed via infusion port 3330 or through a different port (not shown). Balloon member 3320 may be optionally deflated and positioned adjacent other portions of the fibrin sheath as needed (not shown) and optionally other flushing of contrast materials may be performed for further verifications. The contrast enhancing material CM may be dispersed such that to allow visualization substantially beyond the fibrin sheath for visualizing other vasculature portions such as the internal jugular vein JV for example in order to see if it is patent for future access and catheter placement. After proper disruption of the fibrin sheath, imagery verifications and other treatment steps as needed, balloon catheter 3300 can be removed and replaced with a second (new) dialysis catheter 3400.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for disrupting a fibrin sheath from a blood vessel and visualizing thereof, the method comprising:
   introducing a dilation balloon catheter into the blood vessel, the dilation balloon catheter including a dilatation balloon and an infusion lumen having an infusion opening;
   positioning the dilatation balloon adjacent to at least a portion of the fibrin sheath;
   inflating the dilatation balloon to disrupt at least the portion of the fibrin sheath and occlude the blood vessel;
   injecting a contrast enhancing material through the infusion opening and into blood vessel while the dilatation balloon is inflated and is occluding the blood vessel to enable visualization of at least the portion of the fibrin sheath; and
   imaging the blood vessel to verify disruption of at least the portion of the fibrin sheath.

2. The method according to claim 1, wherein the infusion opening opens laterally from the infusion lumen.

3. The method according to claim 1, wherein the infusion opening is positioned proximal to the dilatation balloon.

4. The method according to claim 1, wherein the blood vessel is a superior vena cava.

5. The method according to claim 1, further comprising:
   removing a first dialysis catheter from the blood vessel before introducing the dilation balloon catheter.

6. The method according to claim 5, wherein removing the first dialysis catheter includes:
   inserting a guide wire into the first dialysis catheter; and
   removing the first dialysis catheter over the guide wire.

7. The method according to claim 5, further comprising:
   replacing the dilation balloon catheter with a second dialysis catheter.

8. The method according to claim 1, wherein the infusion opening is located adjacent to the dilation balloon.

9. The method according to claim 1, further comprising:
   dispersing a thrombolytic agent through the infusion lumen.

10. The method according to claim 1, further comprising:
    deflating the dilatation balloon;
    repositioning the dilation balloon adjacent a different portion of the fibrin sheath; and
    repeating at least one of inflating the dilatation balloon, injecting the contrast enhancing material, and imaging of the blood vessel.

11. The method according to claim 1, comprising:
    flushing the contrast enhancing material to disperse beyond the fibrin sheath; and
    visualizing a vasculature portion other than the blood vessel.

12. The method according to claim 11, wherein the vasculature portion includes an internal jugular vein.

13. The method according to claim 11, further comprising:
    operating a valving mechanism disposed in the infusion lumen distally of the infusion opening, wherein injection of the contrast enhancing material follows operation of the valving mechanism such that injection of the contrast enhancing material causes the contrast enhancing material to primarily exit through the infusion opening.

14. The method according to claim 1, wherein the infusion lumen includes a proximal opening and a distal opening that is distal of the dilatation balloon.

15. The method according to claim 14, the method further includes:
    inserting a guidewire into the blood vessel; and
    inserting the dilation balloon catheter such that the guidewire extends into the infusion lumen from the distal opening to the proximal opening.

16. The method according to claim 15, wherein the guidewire is configured to block a distal portion of the infusion lumen, such that injection of the contrast enhancing material causes the contrast enhancing material to primarily exit through the infusion opening.

17. The method according to claim 1, wherein inflating the dilatation balloon includes elevating a pressure in the dilatation balloon to a maximal pressure up to 20 atmospheres.

18. The method according to claim 17, wherein inflating the dilatation balloon further includes maintaining the maximal pressure for at least one minute.

* * * * *